United States Patent
Boyd et al.

(10) Patent No.: US 10,032,343 B2
(45) Date of Patent: *Jul. 24, 2018

(54) SMART HOME DEVICE PROVIDING INTUITIVE ILLUMINATION-BASED STATUS SIGNALING

(71) Applicant: Google LLC, Mountain View, CA (US)

(72) Inventors: Jeffrey A. Boyd, Novato, CA (US); James B. Simister, San Francisco, CA (US); Adam D. Mittleman, Redwood City, CA (US); John B. Filson, Mountain View, CA (US); Fred Bould, Menlo Park, CA (US); David Sloo, Menlo Park, CA (US); Jesse W. Boettcher, Mountain View, CA (US); Anthony M. Fadell, Portola Valley, CA (US); Matthew L. Rogers, Los Gatos, CA (US)

(73) Assignee: Google LLC, Mountain View, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 15/438,076

(22) Filed: Feb. 21, 2017

(65) Prior Publication Data

US 2017/0162007 A1     Jun. 8, 2017

Related U.S. Application Data

(63) Continuation of application No. 14/508,182, filed on Oct. 7, 2014, now Pat. No. 9,613,525.

(Continued)

(51) Int. Cl.
*G08B 5/36* (2006.01)
*H04L 12/28* (2006.01)
(Continued)

(52) U.S. Cl.
CPC ............ *G08B 5/36* (2013.01); *G08B 29/185* (2013.01); *H04L 12/282* (2013.01); *H04L 67/24* (2013.01); *H04L 67/025* (2013.01)

(58) Field of Classification Search
CPC ...... G08B 29/02; G08B 29/04; G08B 25/008; G08B 25/08; G08B 21/14; G08B 21/18;
(Continued)

(56) References Cited

U.S. PATENT DOCUMENTS 7,649,472 B1    1/2010   Paterno
8,172,154 B1    5/2012   Figley et al.
(Continued)

OTHER PUBLICATIONS

Non-Final Office Action dated Jun. 24, 2016, for U.S. Appl. No. 14/508,302, 30 pages.
(Continued)

*Primary Examiner* — Mirza Alam
(74) *Attorney, Agent, or Firm* — Kilpatrick Townsend & Stockton LLP

(57) ABSTRACT

Various methods and systems for smart home devices are presented. Such smart home devices may include one or more environmental sensors that are configured to detect the presence of one or more environmental conditions. Such smart home devices may include a light comprising a plurality of lighting elements. Such a light may be configured to illuminate using a plurality of colors and, possibly, a plurality of animation patterns. Such smart home devices may include a processing system configured to cause the light to illuminate using the plurality of colors and the plurality of animation patterns in response to a plurality of states of the smart home device.

15 Claims, 26 Drawing Sheets

Related U.S. Application Data

(60) Provisional application No. 61/887,969, filed on Oct. 7, 2013, provisional application No. 61/887,963, filed on Oct. 7, 2013.

(51) Int. Cl.
  *G08B 29/18*    (2006.01)
  *H04L 29/08*    (2006.01)

(58) Field of Classification Search
  CPC .... G08B 21/182; G08B 17/117; G08B 21/12; G08B 17/10; G08B 17/107; G01N 33/0031; G01N 33/004
  See application file for complete search history.

(56) References Cited

U.S. PATENT DOCUMENTS

| | | | | |
|---|---|---|---|---|
| 2003/0234725 | A1* | 12/2003 | Lemelson | G08B 7/066 340/521 |
| 2004/0140892 | A1 | 7/2004 | Hanood | |
| 2005/0253709 | A1* | 11/2005 | Baker | G08B 25/009 340/539.26 |
| 2008/0291037 | A1* | 11/2008 | Lax | G08B 7/066 340/628 |
| 2010/0271220 | A1* | 10/2010 | Pattok | G08B 3/10 340/628 |
| 2012/0126975 | A1 | 5/2012 | Gonzales | |
| 2013/0008787 | A1* | 1/2013 | Mammoto | G08B 17/10 204/407 |
| 2013/0093594 | A1* | 4/2013 | Brigham | G08B 17/10 340/628 |
| 2014/0085093 | A1* | 3/2014 | Mittleman | H04L 12/282 340/628 |
| 2015/0054652 | A1* | 2/2015 | Crochet | G08B 5/36 340/815.4 |
| 2015/0077737 | A1* | 3/2015 | Belinsky | G01N 15/0211 356/51 |

OTHER PUBLICATIONS

U.S. Appl. No. 61/863,990, filed Aug. 9, 2013, Inventor Mark Belinsky, et al, all pages.

"Дtektop Дima Gira Rauchmelder" retrieved from https://www.youtube.com/watch?v=NMtcvEhIXG8 on Oct. 12, 2016, all pages.

* cited by examiner

| Color | Meaning |
|---|---|
| (vertical lines) | Hello / confirmation / message |
| (crosshatch) | Everything's "Ok" |
| (diagonal lines) | Something may be wrong |
| (horizontal lines) | Something is definitely wrong |
| (dotted) | Let me help you |

1210

| Animation | Meaning |
|---|---|
| (concentric circles) | "Here's my status" |
| (spinning arc) | "I need your attention" |
| (striped sphere) | "Ok" |
| (flower shape) | "Hi" |

1220

| Speed | Meaning |
|---|---|
| SLOW | Low urgency |
| FAST | Increased urgency |
| ALARM | Maximum urgency |

| Color | Pulse ⊙ | Rotate ↻ | Wave | Shimmer | On/Off ⊙ |
|---|---|---|---|---|---|
| 1251 | Alarm or test | | | | |
| 1252 | Heads Up | Battery Low<br>Battery Critical | | | |
| 1253 | Lights out (no problems) | Connected to client<br>Test completed (all OK)<br>Post-alarm (All Right) | | | |
| 1254 | Choose Language<br>Button Pressed<br>Doorbell<br>Lights out (problems exist) | Ready for connections<br>Countdown to test<br>Reset<br>Shutdown begin<br>Shutdown countdown | Problem Description | Starting up | |
| 1255 | | | | | Night Light |

| Category | Name | Type | LED Behavior | | | Tone | Voice |
|---|---|---|---|---|---|---|---|
| | | | Animation | Color | Timing | | |
| Setup | Boot | State | Pulse | ⊖ | once | Next chime | Hi from Nest.<br>Nest vous souhaite le bonjour. |
| | Language Select | State | Rotate | ⊖ | once per language, pause between, repeat (up to four times) | | Press the button now for English.<br>Appuyer maintenant pour continuer en français. |
| | Ready for Connections | State | Rotate | ⊖ | up to two minutes | | Ready [in the living room]. Press to test. |
| | Setup in Progress | Event | Rotate | ⊖ | while state asserts | | N/A |
| | Connected to Internet | Event | Rotate | ⊘ | once | slow | Connected to the Internet. |
| | Setup Complete | Event | Pulse | ⊘ | once | slow | Ready [in the living room]. |

| Category | Name | Type | LED Behavior | | Timing | Variation | Tone | Voice |
|---|---|---|---|---|---|---|---|---|
| | | | Animation | Color | | | | |
| Manual Test | Button Pressed | Event | Pulse | ◯ | once | alarm | | N/A |
| | Button Pressed for Test | Event | Pulse | ◯ | once | alarm | | N/A |
| | Countdown to Test | State | Rotate | ◯ | until test begins | | | This is only a test. The alarm will sound. The alarm is loud. The test starts in ten seconds. Ten. Nine. Eight. Seven. Six. Five. Four. Three. Two. One. Press or speak stop to cancel. |
| | Cancelled by pressing | Event | Pulse | ◯ | once | alarm | | Cancelled. |
| | Smoke test underway | State | Pulse | ◐ | while state exists | alarm | Alarm | Testing smoke. |
| | CO test underway | State | Pulse | ◐ | while state exists | alarm | Alarm | Testing carbon monoxide. |
| | CO test completing | State | Pulse | ◐ | while state exists | alarm | Alarm | Finishing the test. Just a moment. |
| | Button Pressed While Test Completing | Event | Pulse | ◐ | once, then resumes pulsing on alarm rate | fast | | Finishing the test. Just a moment. |
| | Test Completed, Failed | Event | Pulse | ⊗ | while speech is audible | fast | | The sensors have failed. Replace Nest Protect now. |
| | Test Completed, All OK | Event | Pulse | ⊘ | once | slow | | The test is finished. Everything is okay (in the kitchen). |

FIG. 13B

| Category | Name | Type | LED Behavior Animation | LED Behavior Color | Timing | Verbose | Tone | Voice |
|---|---|---|---|---|---|---|---|---|
| Heads-Up and Alarms | Heads-Up (Level 1) | State | Pulse | ⊗ | while state exists | | | Heads-Up. There's [carbon monoxide] [in the basement]. |
| | Heads-Up (Level 2) | State | Pulse | ⊗ | while state exists | fast | | Heads-Up. There's [smoke] in the [bedroom]. It's getting worse. |
| | Smoke Alarm | State | Pulse | ⦵ | while state exists | alarm | Three long beeps | Emergency. There's [smoke] [in the ...]. |
| | Carbon Monoxide Alarm | State | Pulse | ⦵ | while state exists | alarm | Four short beeps | Emergency. There's [Carbon monoxide] [in the kitchen]. Move to fresh air. |
| | Multi-Criteria Alarm | State | Pulse | ⦵ | while state exists | alarm | Three long beeps | Emergency. There's [smoke] [in the kitchen]. |
| Person and Wave Detection | I See You (Heads-Up, Manual Test Before Simulated Alarms) | State | Nod/Sold | active color | while state exists | | | [About test]: Press or wave to cancel. [Heads-Up pre-alarm]: Press or wave to hush. |
| | Wave Detected (Manual Test Before Simulated Alarms) | Event | Wave | ⊖ | once | out | | Canceled. |
| | Wave Detected (Heads-Up) | Event | Wave | ⊗ | once | out | | [Smoke alarm] hushed [in the living room]. |
| | Wave Detected (Alarm, Simulated Alarm During Manual Test) | Event | Wave | ⊗ | once | | | Hushed Alarm [Smoke] alarm hushed [in the living room]. [Manual test]: Canceled. |
| | Wave Detected (Problem Exists) | Event | Wave | ⊗ | once | | | The Nest Protect batteries are low [upstairs]. Replace the batteries soon. |
| Hushed | Hushed (Heads-Up, Level 1) | State | Pulse | ⊗ | once every 5 seconds while state exists | | | |
| | Hushed (Heads-Up, Level 2) | State | Pulse | ⊗ | once every 3 seconds while state exists | fast | | [Smoke alarm] hushed [in the living room]. |
| | Hushed (Alarm) | State | Pulse | ⦵ | once every 2 seconds while state exists | alarm | | |

FIG. 13C

| Category | Name | Type | LED Behavior | | Tone | Voice |
|---|---|---|---|---|---|---|
| | | | Animation | Color | Timing | Variation | | |
| Post-Alarm | All OK | Event | Pulse | ◈ | once | slow | Chime | [Shhhh] is sleeping [in the bedroom]. |
| Nightly Premises | All OK | Event | Pulse | ◈ | once | slow | | N/A |
| | Problem Exists | State | Pulse | ◈ | four times | | | N/A |
| | Problem Explanation | State | Pulse | ◈ | while speech is audible | default or test | | [Problem description] |
| | Pathlight | Event | Ramp On/Off | ⋯ | see specs for behavior | | | N/A |
| Doorbell | Doorbell Ring | Event | Pulse | ⊖ | once | | Doorbell chime | N/A |
| Reset | Erase All Settings | State | Rotate | ◈ | while state exists | | | Erasing all settings in ten seconds. Press to cancel. Ten, Nine, Eight, Seven, Six, Five, Four, Three, Two, One. Erasing all settings. |
| Software Update | USB Software Update in Progress | State | Rotate | ◈ | while state exists | | | N/A |
| PIR Calibration | PIR Calibration in Progress | State | Rotate | ◈ | while state exists | | | Measuring the room. Just a moment. |
| | PIR Calibration Complete | Event | Pulse | ◈ | once | slow | | N/A |
| Line Power Indicator | Line Power Indicator | State | On | ⊖ | always | | | N/A |
| Critical Problems | Battery Critical | State | None | N/A | N/A | | Chirp every 60 seconds | N/A (Batteries too depleted for voice functions) |
| | Sensor Failure | State | None | N/A | N/A | | Chirp every 60 seconds | [Whom move detected] The sensors have failed [to the bedroom]. Replace Nest Protect now. |
| | Product Expired | State | None | N/A | N/A | | Double chirp every 60 seconds | [Whom move detected] Nest Protect has expired. Replace Nest Protect now. |

FIG. 13D

SMART HOME DEVICE PROVIDING INTUITIVE ILLUMINATION-BASED STATUS SIGNALING

CROSS-REFERENCES TO RELATED APPLICATIONS

This application claims is a continuation of U.S. Non-Provisional application Ser. No. 14/508,182, filed Oct. 7, 2014 entitled "Hazard Detection Unit Providing Intuitive Illumination-Based Status Signaling," which claims priority to U.S. Provisional Application No. 61/887,969, filed Oct. 7, 2013 entitled "User-Friendly Detection Unit," and claims priority to U.S. Provisional Application No. 61/887,963, filed Oct. 7, 2013 which are each hereby incorporated by reference for all purposes.

FIELD

This patent specification relates to systems, devices, methods, and related computer program products for smart buildings including the smart home. More particularly, this patent specification relates to detection units, such as hazard detection units (e.g., smoke detectors, carbon monoxide sensors, etc.) or other monitoring devices, that are useful in smart building and smart home environments.

BACKGROUND

Hazard detectors use sensors to detect substances in the air that may be harmful or that may indicate the development of a hazardous situation. For example, carbon monoxide (CO) and radon gas are substances that can be harmful to humans and animals if exposed to high amounts. However, these substances are difficult to detect with the human senses because they are colorless, odorless, and tasteless. A hazard detector can detect the presence of these substances and prevent the harmful effects of exposure by alarming to notify a user. In other instances, a substance such as smoke, while not necessarily harmful in and of itself, can indicate the development of a hazardous situation, such as fire. An early alarm of the presence of such a substance can prevent the hazardous situation from developing or minimize the harmful effects of the situation. Interconnected hazard detectors include detectors that are connected to a network, enabling communication between the detectors or with a central control unit. This provides several advantages over stand-alone detectors, including the ability to activate multiple alarms when a single detector is triggered. Hazard detectors may be certified under standards defined by governing bodies and/or by companies that perform safety testing, such as Underwriters Laboratories (UL). For example, certain UL standards define thresholds for when smoke detectors and CO detectors should sound an alarm. Certain UL standards also define the required characteristics of the alarm, such as powering requirements and the volume, pitch, and pattern of the alarming sound.

SUMMARY

Various methods, systems, devices, computer-readable mediums that cause one or more processors to perform the methods, an apparatuses are presented. In some embodiments, a hazard detector is present. The hazard detector may include a case, the case having an interior and a plurality of exterior surfaces, wherein the interior of the case houses components of the hazard detector, a first exterior surface of the plurality of exterior surfaces is configured to mount with a wall or ceiling, and a second exterior surface of the plurality of exterior surfaces, located on an opposite side of the case from the first exterior surface. The hazard detector may include a plurality of hazard sensors housed in the interior of the case, the plurality of hazard sensors detect the presence of a plurality of types of hazards. The hazard detector may include a user input component to receive user input, the user input component being located on the second exterior surface of the case. The hazard detector may include a light that emits light, the light comprising a plurality of lighting elements. The light may be capable of illuminating in a plurality of colors and a plurality of animation patterns. When the plurality of lighting elements is illuminated, light output by the light may encircle the user input component. The hazard detector may include a processing system in communication with the plurality of hazard sensors, the user input component, and the light. The processing system may determine a state of the hazard detector. The processing system may cause the light to illuminate using at least one color of the plurality of colors and an animation pattern of the plurality of animation patterns in response to the determined state of the hazard detector.

Embodiments of such a hazard detector may include one or more of the following features: The hazard detector may include a presence sensor wherein the processing system is in communication with the presence sensor. The processing system may be further configured to: receive information indicative of a user presence from the presence sensor while causing the light to illuminate using the at least one color and the animation pattern; and alter the animation pattern used to illuminate the light in response to receiving the information indication of the user presence. The hazard detector may include a microphone. The processing system may be in communication with the microphone and the processing system may be further configured to: receive audio data from the microphone while causing the light to illuminate using the at least one color and the animation pattern; and modulate illumination of the light based on the received audio data from the microphone. The processing system may be configured to module illumination of the light based on a volume of a user's voice received by the microphone. The processing system may access a stored lookup table that relates the plurality of states to the plurality of colors and the plurality of animations. The processing system may identify the at least one color associated with the determined state and the animation pattern associated with the determined state. The plurality of animations may comprise a rotating animation in which lighting elements of the plurality of lighting elements are sequentially increased and decreased in brightness around the ring-shaped light. The light may include a light ring that receives and disperses light generated by the plurality of lighting elements, wherein the light ring comprises a plurality of recessed regions, wherein a lighting element of the plurality of lighting elements is proximate to a recessed region of the plurality of recessed regions. The plurality of lighting elements may include a plurality of light emitting diodes (LEDs) and each LED is positioned within a recess created by the plurality of recessed regions. The light output by the ring-shaped light may substantially define an edge of the user input component. The plurality of LEDs can be located between the user input component and the first exterior surface of the case of the hazard detector. The hazard detector may include a passive infrared (PIR) detector, wherein the PIR detector is configured to sense infrared light through the button, wherein the button is configured to function as a lens.

A method for illuminating a light of a hazard detector may be presented. The method may include determining, by the hazard detector, a state of the hazard detector. The method may include accessing, by the hazard detector, a stored lookup table that relates a plurality of states of the hazard detector to a plurality of colors and a plurality of animations. The method may include identifying, by the hazard detector, using the stored lookup table, at least one color associated with the determined state and the animation pattern associated with the determined state. The method may include causing, by the hazard detector, the light of the hazard detector to illuminate using the identified at least one color of the plurality of colors and the identified animation pattern of the plurality of animation patterns.

A hazard detector apparatus may be presented. The hazard detector apparatus may include means for detecting a presence of a hazard. The hazard detector apparatus may include means for determining a state of the hazard detector apparatus, wherein the means for determining the state of the hazard detector apparatus comprises checking a status of the means for detecting the presence of the hazard. The hazard detector apparatus may include means for accessing a storage means that relates a plurality of states of the hazard detector apparatus to a plurality of colors and a plurality of animations. The hazard detector apparatus may include means for identifying, using the storage means, at least one color associated with the determined state and the animation pattern associated with the determined state. The hazard detector apparatus may include means for causing a lighting means of the hazard detector apparatus to illuminate using the identified at least one color of the plurality of colors and the identified animation pattern of the plurality of animation patterns.

BRIEF DESCRIPTION OF THE DRAWINGS

FIG. 12A illustrates embodiments of definitions for visual effects that may be used by a hazard detector.

FIG. 12B illustrates various combinations of visual effects and color that may be used by a hazard detector.

FIGS. 13A-13D represent various variations on how a light of a hazard detector may be illuminated to communicate information to a user.

DETAILED DESCRIPTION

Providing intelligent information to a person in the vicinity of a hazard detector may be accomplished via a light that has a variety of modes. For instance, a light of a hazard detector may output multiple colors (either at different times or simultaneously), multiple animations, and/or present such animations at various speeds in response to different states and/or events of the hazard detector. Such a light may allow a user to discern a significant amount of information from the hazard detector quickly and/or without the hazard detector making noise. Further, such a light may provide a user with guidance as to how physical input can be provided by a user to the hazard detector: in some embodiments, light is output in the form of a ring that encircles a button. By the user pressing the hazard detector within the ring of light, the user may provide input to the hazard detector via the button. Such an arrangement may be especially beneficial in a darkened environment. Therefore, the light may provide an indication of a state of the hazard detector while also illuminating the location of the button for receiving user input.

The light of such a hazard detector may use a light guide such that a finite number of lighting elements (e.g., light emitting diodes) may be used to produce a continuous or nearly continuous ring of light output from the hazard detector. For example, internal to the hazard detector behind the button, at least a portion of the light guide may be installed, such that lighting elements located behind the button, or otherwise within the hazard detector, can be used to output light via the light guide such that it appears to a user as a ring. The button may also conceal a sensor, such as a passive infrared (PIR) sensor and, possibly, a lens. Accordingly, a user may press the button to provide input, while the user's presence in front of the button may be sensed by the hazard detector.

Figure 1:
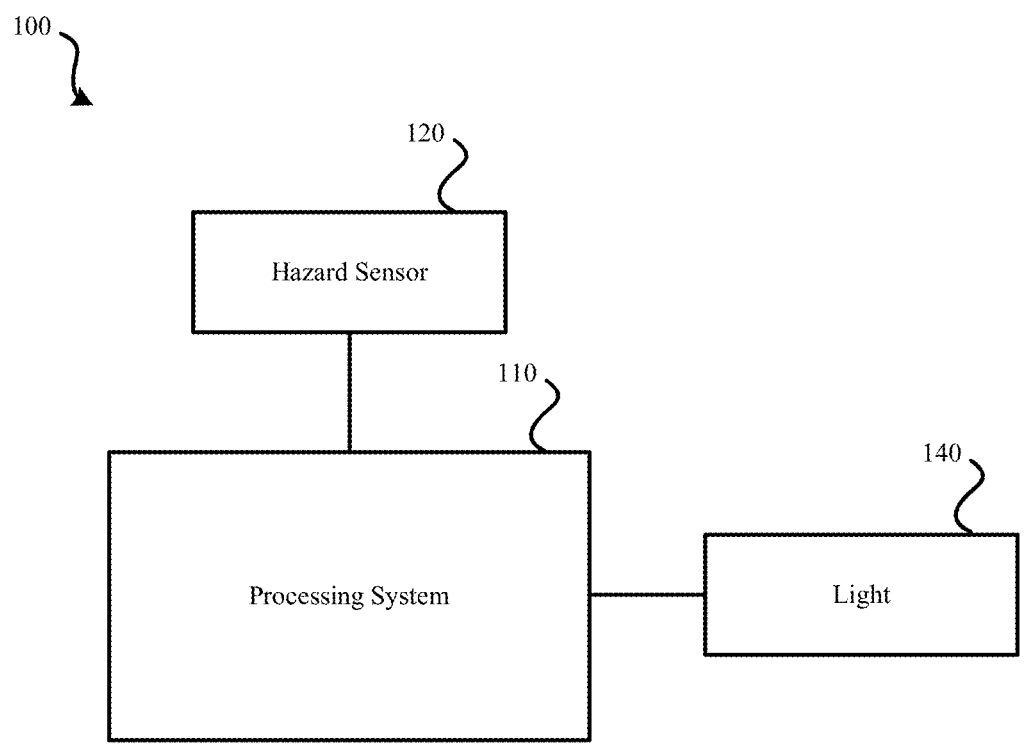
FIG. 1 illustrates an embodiment of a hazard detector that outputs information via a light.

FIG. 1 illustrates an embodiment of a hazard detector 100 that presents information via a light. Hazard detector 100 may include processing system 110, hazard sensor 120, and light 140. It should be understood that additional components may be present and are not illustrated for simplicity of understanding. For instance, hazard detector 100 may include one or more power sources and a case to house components of the hazard detector.

Processing system 110 may include one or more processors. Processing system 110 may receive input from hazard sensor 120 and/or other sources. Based on input from hazard sensor 120 and/or other sources, processing system 110 may cause light 140 to illuminate using various illumination modes. In some embodiments, processing system 110 includes at least two processors: a low-level processor and a high-level processor. The low-level processor may handle functions related to hazard detection and may be communicatively connected with hazard sensor 120. A high-level processor, which may be configured to handle functions related to user input, wireless communication, and usability may control illumination of light 140. In some embodiments, both the high and low level processors are able to cause light 140 to illuminate. Such processing may be divided between the high and low level processor such that functions of processor system 110 related to hazard detection are substantially isolated from other functions directed to usability. For instance, the low level processor may be able to cause an alarm to sound if a hazardous condition is present even if the high level processor is not functioning properly.

Hazard sensor 120 may represent a smoke sensor or a carbon monoxide sensor. In other embodiments, hazard sensor 120 may represent some other form of sensor that detects a hazard in the environment of hazard detector 100. While a single hazard sensor 120 is illustrated as present in hazard detector 100, it should be understood that in various embodiments multiple hazard sensors may be present, such as a carbon monoxide sensor and a smoke sensor. Further, multiple types of smoke sensors may be present, such as an ionization-based smoke sensor and/or a photoelectric-based smoke sensor. Hazard sensor 120 may be communicatively connected with processing system 110 such that, when a hazard is detected by hazard sensor 120, processing system 110 receives input from the sensor indicative of the hazard.

Light 140 may represent a light integrated into hazard detector 100 that outputs light to the external environment around hazard detector 100 based on input from processing system 110. Light 140 may include one or more lighting elements, such as light emitting diodes (LEDs). Light 140 may output various illumination modes that can include: multiple colors, multiple animation patterns, and/or such multiple animation patterns at varying speeds. The color(s), animation pattern, and speed of animation output by light 140 may be determined based on input received from processing system 110. Therefore, based on the state of hazard detector 100, the color(s), animation pattern, and/or speed of the animation output by light 140 may vary.

Figure 2:
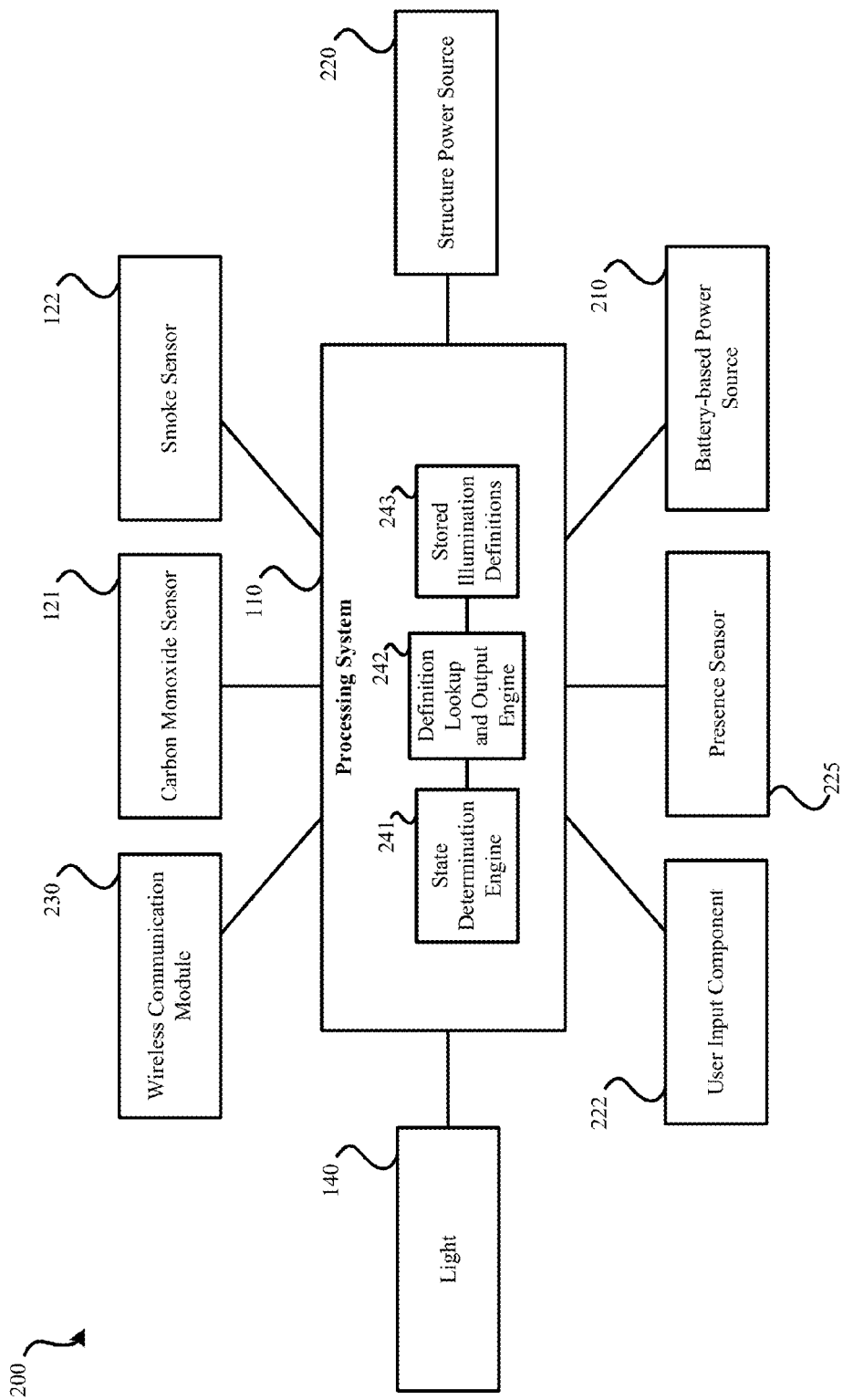
FIG. 2 illustrates another embodiment of a hazard detector that presents information via a light.

It should be understood that the block diagram presented in hazard detector 100 in FIG. 1 is highly simplified. As such, components that are not illustrated may be present, such as a power source, case, light guide, etc. FIG. 2 illustrates another embodiment of a hazard detector that has a light. Hazard detector 200 may represent a more detailed embodiment of hazard detector 100 of FIG. 1. In hazard detector 200, various components may be present including: processing system 110, light 140, carbon monoxide sensor 121, smoke sensor 122, battery-based power source 210, wireless communication module 230, user input component 222, and presence sensor 225. Additional components may also be present, such as a microphone and ultrasonic sensor (e.g., for detection of movement).

Processing system 110 of hazard detector 200 may include multiple modules. Such modules may be implemented using hardware, firmware, or software that is executed by hardware. Such modules may include: state determination engine 241, definition lookup and output engine 242, and stored illumination definitions 243. For instance, such modules may be executed by a high-level processor or a low-level of hazard detector 200. State determination engine 241 may be configured to determine the state of hazard detector 200 and determine when it is appropriate to illuminate light 140. The state determined by state determination engine 241 may be used to determine at least one color, animation, and/or speed for the animation to be used by light 140. The state determined by state determination engine 141 may be passed to definition lookup and output engine 242. Definition lookup and output engine 242 may use the received state to access stored illumination definitions 243. Stored illumination definitions 243 may be stored on a non-transitory computer readable medium, such as a ROM or flash memory that is functionally a part of processing system 110. Stored illumination definitions 243 may be in the form of one or more lookup tables or one or more databases that use the determined state to select: one or more colors, an animation, and/or a speed. In stored illumination definitions 243, various colors, animations, and/or speeds of animations may be stored in association with various states. Therefore, definition lookup and output engine 242 may use the state determined by state determination engine 241 in combination with stored illumination definitions 243 to identify: one or more colors, an animation, and/or speed of animation to use to illuminate light 140. Further, in some embodiments, stored illumination definitions 243 may indicate an amount of time for which light 140 should be illuminated based on the state determined by state determination engine 241. Definition lookup and output engine 242 may provide an output to light 140 (or some other component of the hazard detector) that causes light 140 to illuminate according to the one or more colors, the animation, and/or the speed of animation determined based on the state.

Light 140 may function as detailed in relation to hazard detector 100. In hazard detector 200, two hazard sensors are present: carbon monoxide sensor 121 and smoke sensor 122. In some embodiments, multiple versions of each of these types of sensors can be present. For instance, an ionization and a photoelectric smoke sensor may be present in hazard detector 200. When carbon monoxide sensor 121 senses carbon monoxide or smoke sensor 122 senses smoke, indication may be sent to a processor of processing system 110. This indication may be transmitted to a low-level processor that triggers an alarm to sound. This low-level processor may trigger light 140 directly to illuminate in a state indicative of a hazard or may provide input to a high-level processor that is part of processing system 110 that triggers a lookup of an illumination definition via stored illumination definitions 243 to determine an appropriate color, animation, and/or speed of animation to use for illumination of light 140. Regardless of whether the high-level or low-level processor is used, a different color, animation, and/or speed may be used for carbon monoxide as compared to smoke. In some embodiments, both the low and high level processors are capable of causing light 140 to illuminate.

Wireless communication module 230 may allow processing system 110 to communicate with a wireless network present within the structure in which hazard detector 200 is installed. For instance, wireless communication module 230 may communicate with a wireless network that uses the IEEE 802.11a/b/g network protocol standard for communication. Wireless communication module 230 may permit processing system 110 to communicate with a remote server, which may be maintained by a manufacturer of hazard detector 200 or by a third-party. The remote server may be configured to provide information to processing system 110 about an account of a user associated with hazard detector 200. For instance, if an account of the user maintained at the remote server requires attention from a user, such indication may be provided to processing system 110 via wireless communication module 230. Such indication may be provided by the remote server in response to inquiry from processing system 110 made to the remote server. Further, processing system 110 may transmit status information to a remote server. Such an arrangement may permit a user to view status information about the hazard detector by logging in to the remote server via a computing device and accessing the user account.

User input component 222 may represent a component that receives input that can be passed to processing system 110. User input component 222 may take the form of a button or switch on hazard detector 200. By depressing the button or otherwise actuating user input component 222, a user can provide input via user input component 222 to processing system 110. For instance, user input component 222 may be used by a user to disable the alarm currently sounding by hazard detector 200. User input component 222 may be encircled or have its perimeter otherwise outlined by light 140 (that is, by the light itself and/or by light output by light 140). Therefore, when light 140 is active, and the user desires to provide input, the user may simply touch or push hazard detector 200 within the area defined by light 140 and/or the light output by light 140.

Presence sensor 225 may detect presence in the vicinity of hazard detector 200. Presence sensor 225 may include one or more sensors, such as passive infrared (PIR) sensors. Presence sensor 225 may detect one or more gestures that may be performed by user in the vicinity of hazard detector 200 and/or may detect the presence of one or more users. For instance, presence sensor 225 may detect a wave gesture performed by a user. In some embodiments, multiple waves may be required to be performed by the user in order for a wave gesture to be detected. In some embodiments, presence sensor 225 may only be enabled at certain times, which may conserve power. Such presence detection may be used to enable lighting to allow a user to see in the vicinity of hazard detector 200 and/or may be used to control and/or provide occupancy data to HVAC systems within the structure. Presence sensor 225 may be integrated with user input component 222 such that user input component 222 conceals presence sensor 225. Further, an integrated lens may be present such that presence sensor 225 detects the presence of users through the button of user input component 222.

Hazard detector 200 is illustrated as including battery-based power source 210 and structure power source 220. In some embodiments of hazard detector 200, such a configuration may be present. Structure power source 220 may be used to power hazard detector 200 when such power is present. Structure power source 220 may represent a hard-wired connection within a structure (e.g., house, building, office, etc.) that provides an AC or DC power to one or more hazard detectors located throughout the structure. While the AC or DC power may be available a significant percentage of time (e.g., 99.5% of the time), it may be desirable for hazard detector 200 to continue functioning if structure power is unavailable (e.g., during a power failure). As such, battery-based power source 210 may also be present. Battery-based power source 210 may include one or more batteries which power the various components of hazard detector 200 when structure power source 220 is not available. In some embodiments of hazard detector 200, structure power source 220 is not present. As such, hazard detector 200 may permanently rely on battery-based power source 210 to power components of hazard detector 200. Structure power source 220 and battery-based power source 210 are illustrated in FIG. 2 as connected with processing system 110. Processing system 110 may determine if structure power source 220 is available and/or check a charge level of battery-based power source 210. It should be understood that, while structure power source 220 and battery-based power source 210 are illustrated as only connected with processing system 110, this is for simplicity of illustration only; structure power source 220 and/or battery-based power source 210 may be connected to the various components of hazard detector 200 as necessary to power such components.

Figure 3:
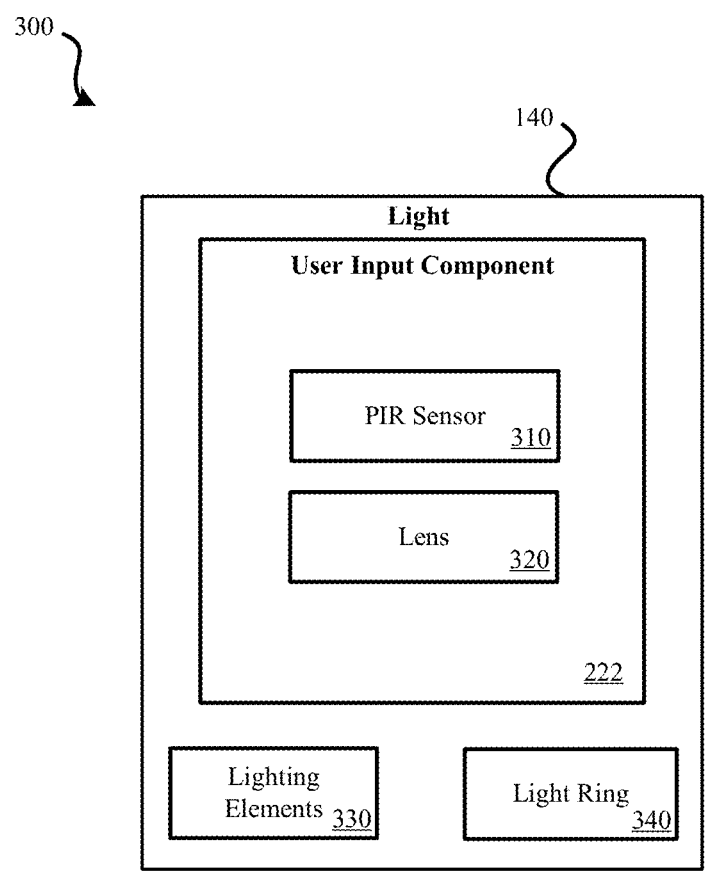
FIG. 3 illustrates an embodiment of a light that encircles a user input component of a hazard detector.

FIG. 3 illustrates an embodiment 300 of a light that encircles a user input component of a hazard detector. Embodiment 300 may represent a block diagram of the light and user input component of FIGS. 1 and 2. Embodiment 300 may be incorporated into various forms of hazard detectors including those described in this document, such as in FIGS. 1 and 2. Embodiment 300 may include light 140, user input component 222, PIR sensor 310, lens 320, lighting elements 330, and light ring 340. Light 140 may be understood as including lighting elements 330 and light ring 340. Lighting elements 330 may include one or more components that outputs light. For instance, lighting elements 330 may be LEDs. In some embodiments, light 140 includes five LEDs functioning as lighting elements 330. It should be understood that in other embodiments, a fewer or greater number of LEDs functioning as lighting elements 330 may be present.

Light 140, as illustrated embodiment 300, may encircle user input component 222. To accomplish this, light ring 340 may be used. Light ring 340, which, more generally, can be referred to as a light guide, may diffuse or otherwise direct light generated by lighting elements 330 to emanate a face of the hazard detector in which embodiment 300 is integrated. Light ring 340 may be a solid piece of transparent or semitransparent material, such as plastic or glass, that causes light emitted by lighting elements 330 to emanate from a hazard detector in approximately a continuous ring of light when all of lighting elements 330 are illuminated. As such, light ring 340 may cause output light to appear from the exterior of the hazard detector of which embodiment 300 is a part to be in the shape of a ring. This ring of light may be circular or oval. Other embodiments of light guides may cause output light to form some other form of perimeter, such as a perimeter of an octagon, quadrilateral, triangle, or some other geometric or abstract shape.

User input component 222, which may be in the form of a button, may be encircled by light output by light 140. More specifically, light output through light ring 340 and/or a portion of light ring 340 may substantially define the edge of user input component 222. As such, a user touching the hazard detector within a perimeter of light output by light ring 340 can be expected to be touching user input component 222. Such an arrangement may be particularly useful in the dark such that, when light is emanating from light ring 340, a user only needs to touch the hazard detector within the light output from light ring 340 in order to press user input component 222.

User input component 222 may be integrated with presence sensor 225 as detailed in relation to hazard detector 200. In embodiment 300, PIR sensor 310 and lens 320 are being used as the presence sensor. PIR sensor 310 may sense the presence of a user based on infrared detection through the face of user input component 222. Incorporated as part of user input component 222 may be lens 320, which helps define a region in the environment of the hazard detector in which PIR sensor 310 can sense the presence of the user and/or a gesture being performed based on received infrared radiation.

Lighting elements 330 and at least a portion of light ring 340 may be located behind the face of user input component 222, similar to PIR sensor 310. As such, lighting elements 330 may generate light behind the face of user input component 222 and light ring 340 may direct such light to a portion of light ring 340 that is present on an exterior face of the hazard detector. Alternatively, light ring 240 may be completely or nearly completely hidden from external view behind user input component 222; light from lighting elements 330 may be directed by light ring 340 to reflect off of a portion of a case (or, more specifically, a cover plate) of the hazard detector, such as a portion of the case that is depressed. Such an arrangement may permit individual lighting elements of lighting elements 330 to not directly face the exterior of the hazard detector. Such an arrangement may be beneficial for space savings within the hazard detector, allowing for a compact configuration.

Figure 4:
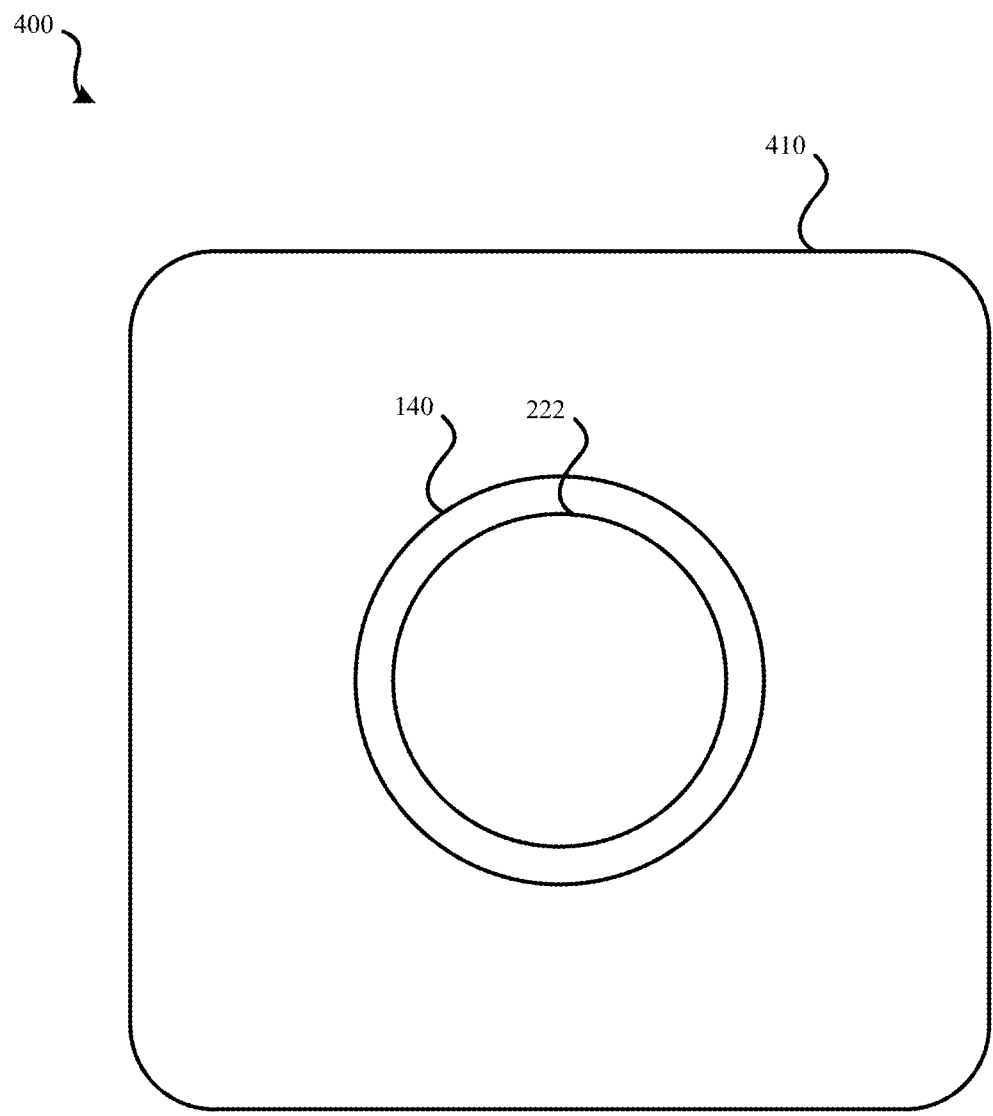
FIG. 4 illustrates an external view of an embodiment of a hazard detector with a ring-shaped light.

FIG. 4 illustrates an external view of an embodiment of a hazard detector 400 with a ring-shaped light. Hazard detector 400 may represent the hazard detectors of FIGS. 1 and 2, and may include the embodiment of FIG. 3. FIG. 4 illustrates an external view of an embodiment of a hazard detector 400. Hazard detector 400 may include case 410, light 140, and user input component 222. Case 410 may represent a shell of hazard detector 400 which is configured to be mounted to a wall or ceiling. Case 410 may allow airflow through hazard detector 400 to permit one or more sensors within hazard detector 400 to be exposed to the air of the ambient environment of hazard detector 400. On the side of case 410 opposite the side used for mounting to a wall or ceiling, light 140 may output light. The portion of light 140 visible in FIG. 4 may be a portion of a light ring that causes light generated by lighting elements hidden within the hazard detector to emanate from a face of case 410. In some embodiments light 140 is concealed within hazard detector 400, but a portion of case 410 (or some other physical portion of the hazard detector) is arranged to reflect light generated by light 140. For instance, a portion of case 410 may be depressed in order to reflect and scatter light output by light 140. More detail regarding case 410 is provided in relation to FIG. 6E; such a case may include a cover plate, front casing, backplate, and/or mounting plate. Light 140 may include one or more light elements, such as LEDs that are behind the face of user input component 222. Light 140 may be configured to present various colors and/or various lighting patterns, possibly with such patterns presented at various speeds.

While light 140 is illustrated as a ring (which can also be referred to as a halo), it should be understood that, in other embodiments of hazard detector 400, other shapes may be used for light 140. For instance, light 140 may be elliptical, square, triangular, some other geometric shape, some other abstract shape, or a line. Similarly, in some embodiments, case 410 is square or rectangular, with rounded edges. While such a design may be especially pleasing to the eye, other shapes, both geometric or abstract, may be used to house the functional components of hazard detector 400. Generation of the light may occur behind user input component 222 and may be directed by a light ring, which may also be located behind user input component 222, to emanate from the hazard detector in the appearance of a ring, as illustrated by the halo-like shape of light 140. As such, in some embodiments, the entire light ring and lighting elements (which, collectively, form light 140) may be located behind user input component 222 and the light directed by the light ring may reflect off of a recessed portion of case 410 into the ambient environment of hazard detector 400 for viewing by a user.

User input component 222 may include a lens that is used in conjunction with a presence sensor (e.g., PIR sensor) to determine if a user is present and/or detect whether a gesture has been performed by user. User input component 222 may have its perimeter substantially defined by the light emanating from light 140. User input component 222 may serve a dual function: functioning as a lens and as a button which can be pushed by user to provide input to hazard detector 400. In some embodiments, user input component 222 is a button but does not include an integrated lens. When user input component 222 is a button, by having user input component 222 encircled by emitted light by light 140, it may be easy for a user to locate the button in a darkened environment when light 140 is illuminated. In such a situation, the user would only need to push within the circle of light (the "halo") or other region defined by light 140 in order to actuate the button.

Light 140 may appear substantially centered on an exterior surface of case 410. Case 410 may be designed for a first exterior surface mount to a wall or ceiling. The opposite exterior surface of case 410 may include light 140. Light 140 and user input component 222 may be substantially centered about an axis extending through the center of the first and second exterior surfaces of case 410 of hazard detector 400. In other embodiments, light 140 and/or user input component 222 may not be centered on the exterior surface of case 410. In some embodiments, light 140 may not be recessed within case 410 or may extend beyond an exterior surface of case 410. For example, in some embodiments, light 140 may be present as a recessed portion of case 410 that permits light generated within case 410 (e.g., behind user input component 222) to emanate from the recessed portion of case 410.

In some embodiments, the location of light 140 is a depressed portion of case 410. From behind user input module 222 or from some other location within case 410, light is emitted into the depressed portion of case 410. The light reflects off of case 410 into the environment of hazard detector 410, outlining user input module 222. Further, due to the depressed portion of case 410, from various angles a user may be able to partially see behind user input module 222. Such a region may also be illuminated by light when light 140 is illuminated.

Figure 5A:
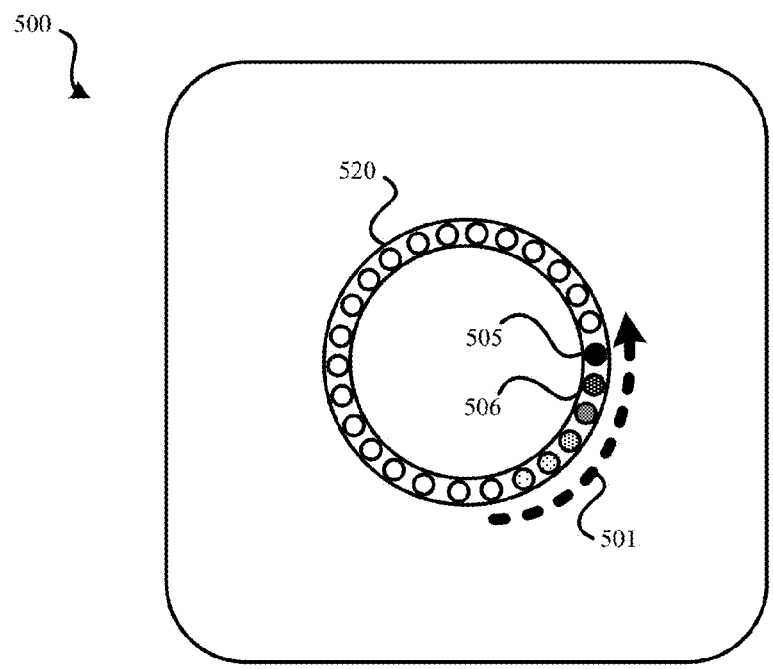
FIGS. 5A and 5B illustrate an external view of an embodiment of a hazard detector that outputs a circular pattern of light.
Figure 5B:
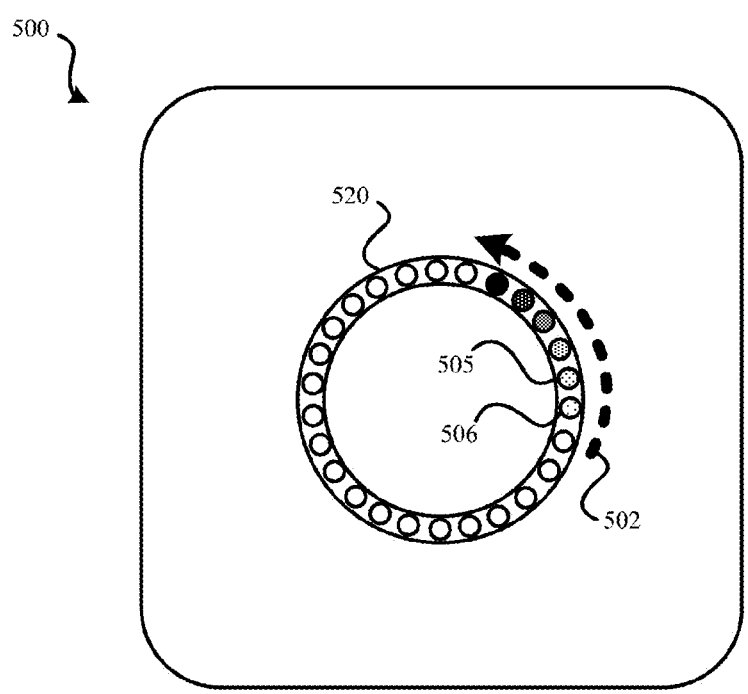

In some embodiments, the light elements of the light of a hazard detector shine directly out of the hazard detector, such as illustrated in FIGS. 5A and 5B. FIGS. 5A and 5B illustrate an external view of an embodiment of a hazard detector 500 that is outputting a circular pattern of light. In hazard detector 500, the lighting elements of light 520 shine directly out of hazard detector 500, the light not being redirected using a light ring. It should be understood that the principles detailed in relation to hazard detector 500 may also be applied to a hazard detector that uses a light ring to direct light to the exterior of the hazard detector. Hazard detector 500, which is illustrated in FIGS. 5A and 5B in two different states of a single animation pattern, may represent any of the hazard detectors detailed in this document. FIGS. 5A and 5B illustrate hazard detector 500 outputting a lighting effect or animation. This lighting effect can be output in a substantially circular pattern and can be referred to as a circulation effect, halo effect, or halo-sweep effect. The darker a lighting element is shaded in FIGS. 5A and 5B, the brighter the lighting element may be illuminated. Therefore, in some embodiments, a first lighting element may be bright, while the lighting element immediately behind it may be slightly less bright, and so on.

The circulation effect can be caused by various lighting elements, such as LEDs, of light 520 being illuminated at different brightness levels at a given time. Lighting elements of light 520 are illuminated consecutively counterclockwise (or, alternatively, clockwise), then faded to off. For example, in FIG. 5A, light element 506 may be lit at a first brightness. Shortly thereafter, light element 505 may be lit at the first brightness level and light element 506 may have its brightness level decreased to a second, lower brightness level. In FIG. 5B, more time has elapsed and the brightness level of light element 505 has been further decreased and the brightness level of light element 506 has also been decreased to a level below that of light element 505. This effect results in the appearance of a point of light "spinning" or "rotating" around light 520 with a tail. A user viewing hazard detector 500 may view the circulation or halo effect and understand the status of the hazard detector based on the lighting effect, the speed of the effect, and/or the color of light being output by light 520. In some embodiments, when the circulation effect is being output by hazard detector 500, each lighting element of light 520 may output the same color, or multiple colors may be output by different lighting elements. Imaginary arrow 501 illustrates the perceived direction of motion of the circulation effect. It should be understood that the opposite direction is also possible and/or that such an effect may be applied to a shape of light other than a halo, such as an ellipse, triangle, square, abstract shape or quadrangle, to name only a few examples. Imaginary arrow 502 shows the perceived position of the circulation effect of hazard detector 500 at a later time at which a different lighting element is now the brightest lighting element with subsequent lighting elements being illuminated progressively less bright.

Hazard detector 500 illustrates a large number of lighting elements being present. While twenty-six light elements are illustrated, it should be understood that this is for exemplary purposes only. Other embodiments may have fewer or greater numbers of lighting elements. For instance, in some embodiments, five lighting elements are present. In general, having a fewer number of light elements may decrease production costs.

Figure 6A:
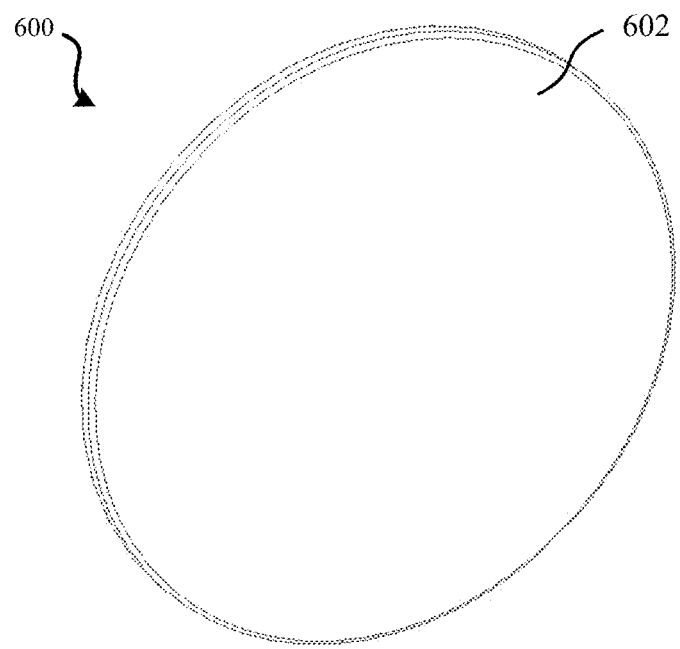
FIGS. 6A and 6B illustrate front and rear perspective views, respectively, of a lens button of an embodiment of a hazard detector.
Figure 6B:
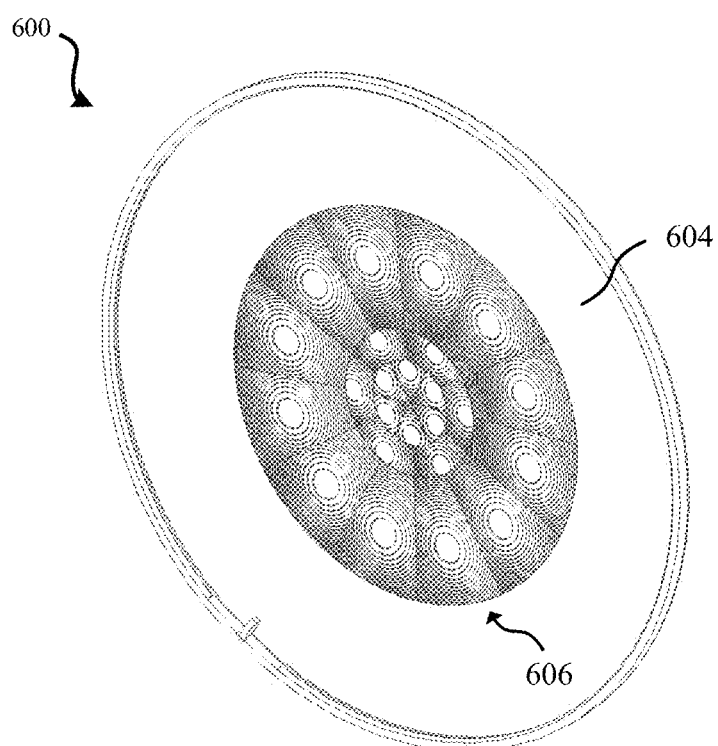

FIGS. 6A and 6B are respectively front and rear perspective views of a lens button 600. Lens button 600 may represent a form of a user input component, such as user input component 222 of FIGS. 2 and 3. Lens button 600 includes a front surface 602 and a rear surface 604. Lens button 600 may be coupled with a front of a case, such as case 410 by attaching lens button 600 to a light ring, such as light ring 340 of FIG. 3, and coupling light ring 340 to case 410. Lens button 600 is configured to be pressed by a user to provide input to a hazard detector on which lens button 600 is mounted and/or for various other purposes, such as quieting an alarm that is sounding. Lens button 600 may be transparent or semi-transparent to one or more sensors positioned behind lens button 600. For example, in one embodiment, at least one PIR sensor is positioned behind lens button 600. The PIR sensor may receive infrared radiation from external objects, such as users, through lens button 600. Such received infrared radiation may be used to determine if an occupant is present within a room in which hazard detector 400 is positioned. To visible light, lens button 600 may be substantially opaque. As such, a user viewing lens button 600 may not be able to see any sensor, such as a concealed PIR sensor, that is located within a hazard detector behind lens button 600. While the above description focuses on the use of a PIR sensor, it should be understood that other forms of sensors may be located behind lens button 600 and may sense through lens button 600.

The rear surface 604 of lens button 600, illustrated in FIG. 6B, may have a Fresnel lens pattern 606 that allows the PIR sensor, or another sensor, positioned behind lens button 600, to view into a room (or other environment) in which the hazard detector is installed further than if no Fresnel lens was present. Fresnel lens pattern 606 may be substantially concentric around the center of the circular lens button 600. In some embodiments, Fresnel lens pattern 606 may include a plurality of concentrically arranged rings that each provides a slightly different viewing cone. Each concentrically arranged ring may provide a progressively larger viewing area or cone than rings concentrically arranged and located radially closer to a central axis of lens button 600. In one embodiment, an internal angle of the viewing cones provided by Fresnel lens pattern 606 may vary from between about 15° and about 150° so as to provide a viewing radius on a floor or wall positioned directly in front of the hazard detector at a distance of approximately 10 feet or between about 0.5 m and about 8.8 m. In this manner, one or more PIR sensors, and/or some other type of sensor, positioned behind lens button 600, may detect the presence of an occupant within a room in which the hazard detector is installed.

In some embodiments, no lens may be present. Therefore, button 600 may function as a transparent or semi-transparent window to one or more sensors, such as a PIR sensor, to allow a user to be detected in the vicinity of the hazard detector. A user viewing lens button 600 may not be able to see such a PIR sensor through lens button 600 due to lens button 600 being substantially opaque to visible light. It should be understood that without a lens, such as Fresnel lens pattern 606 being present, the range at which the PIR sensor can detect the presence of a user based on infrared radiation may be decreased. In some embodiments, a type of lens other than Fresnel may be used. For instance, a type of material semi-transparent to infrared radiation may be used as a form of lens to control a distance at which the PIR sensor can detect a user presence (e.g., the more transparent, the farther a distance away the user may be sensed).

Figure 6C:
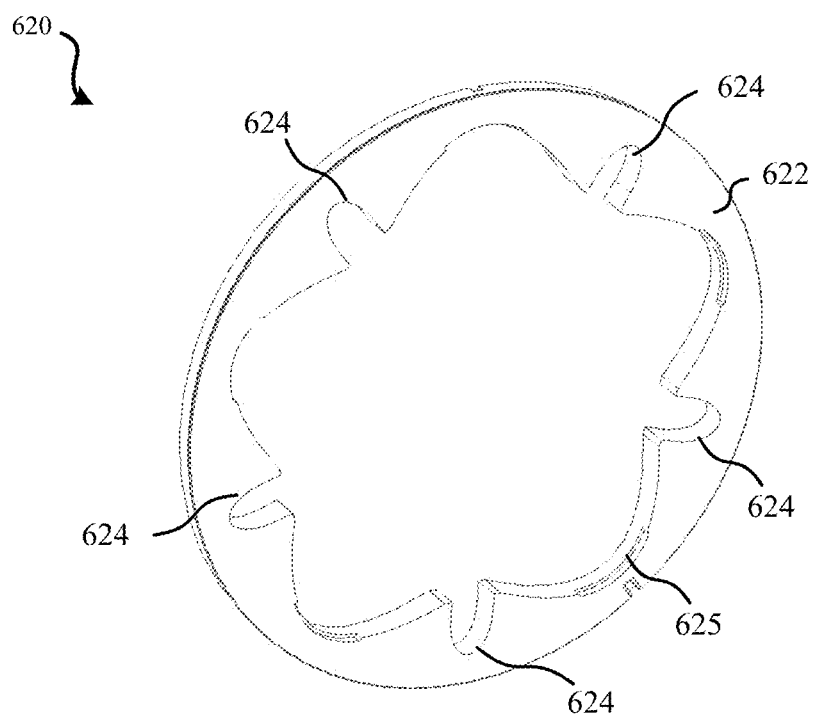
FIGS. 6C and 6D illustrate front and rear perspective views, respectively, of a light guide of an embodiment of a hazard detector.
Figure 6D:
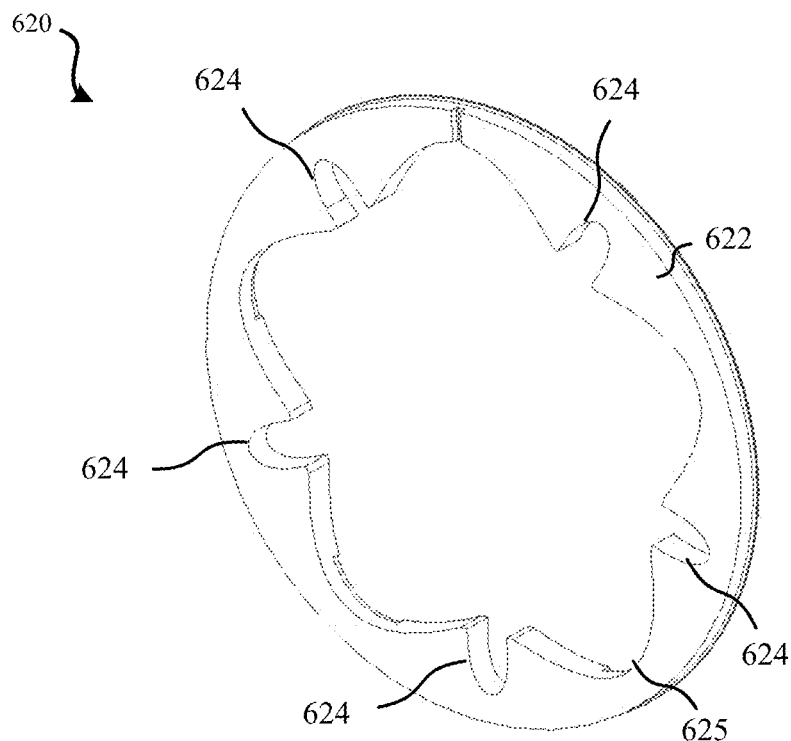

FIGS. 6C and 6D illustrate front and rear perspective views of a light ring 620 that may be used to disperse light provided by lighting elements, such as LEDs. Light ring 620 may be formed from a material such as glass or plastic that is partially or substantially transparent to visible light. In some embodiments, light ring 620 may be semi-transparent, which may be useful in diffusing the light generated by multiple light elements. Light ring 620 may provide for lighting, for example, around lens button 600. Light ring 620 may correspond to light 140 of FIGS. 1 and 2, and/or light ring 340 of FIG. 3. Light ring 620 can include a body portion 622 and may be coupled with lens button 600 via adhesive bonding or some other method known in the art, such as mechanical connection. In turn, light ring 620 may be coupled with a front casing (such as detailed in relation to FIG. 6E) such as by orienting light ring 620 with respect to a surface of a front casing and pressing light ring 620 axially downward relative to a front casing so that recessed portions 625 of light ring 620 mate and couple with tabs (not shown) of the front casing. These tabs may fit over the recessed portions 625 of light ring 620 and secure light ring 620 adjacent a surface of the front casing. Light ring 620 also includes a plurality of second recesses 624 within which a light element (e.g., an LED) or other form of light element may be positioned to illuminate light ring 620. As such, in each recess of the second plurality of recesses, a lighting element may be placed such that light ring 620 disperses the light. In operation, light ring 620 can disperse light provided by the light elements to provide a halo effect behind and around lens button 600.

Figure 6E:
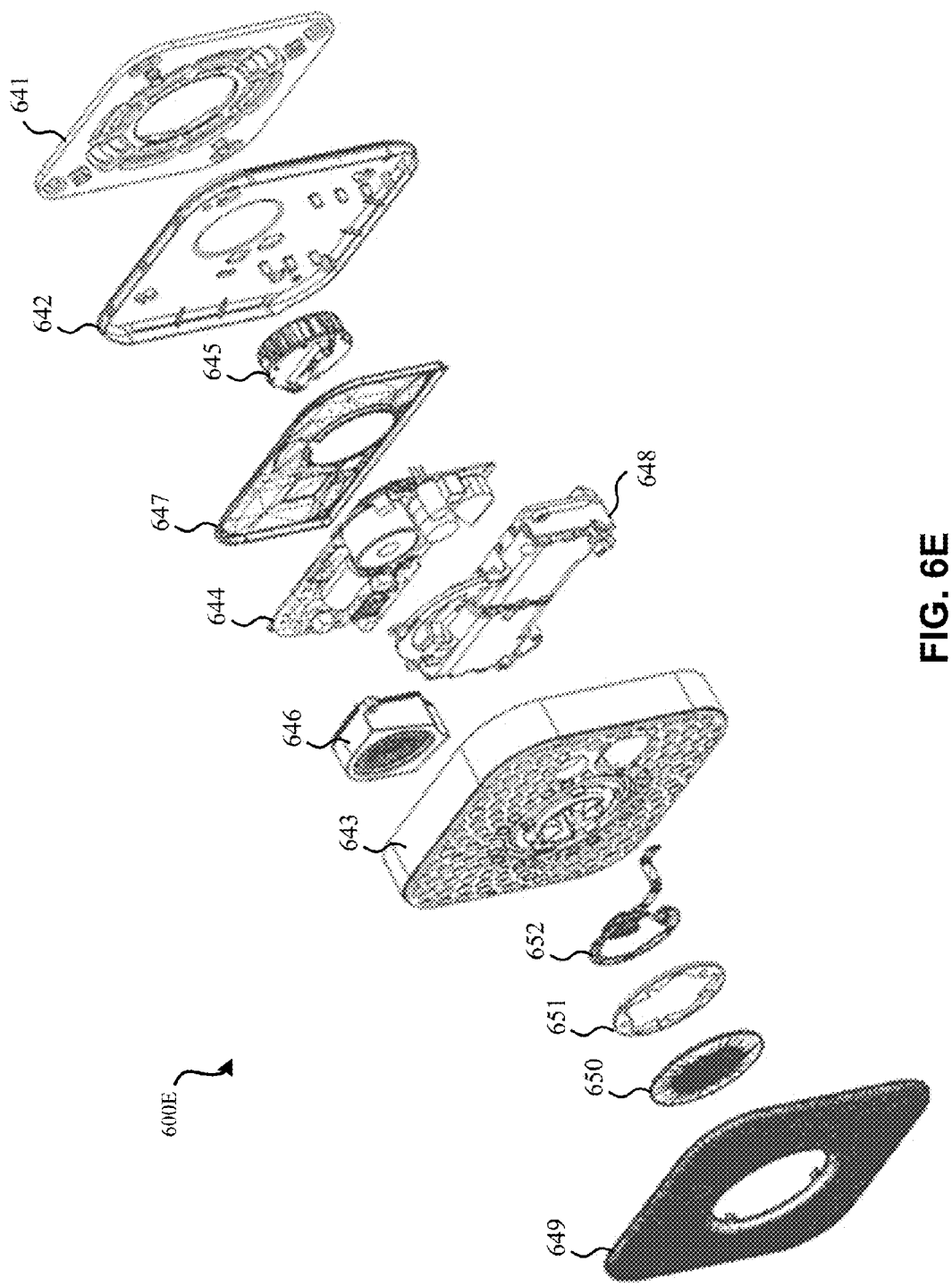
FIG. 6E illustrates a perspective exploded view of an embodiment of a hazard detector that includes a light guide and a ring-shaped light.

In FIG. 6E, an embodiment of a hazard detector 600E is illustrated. Hazard detector 600E represents an exploded view of a hazard detector, such as the hazard detectors detailed herein, including hazard detectors 100 and 200.

In some embodiments, hazard detector 600E is a roughly square or rectangular shaped object having a width of approximately 120 to 134 mm and a thickness of approximately 38 mm. Stated differently, hazard detector 600E is a multi-sensing unit having a fairly compact shape and size that may be easily attached to a wall or ceiling of a home or structure so as to be able, among other functionalities, to detect the presence of smoke and alert an occupant therein of the potential fire danger. As shown in FIG. 6E, hazard detector 600E includes a mounting plate 641 that may be attached to a wall or ceiling of the building or structure to secure the hazard detector 600E thereto. Mounting plate 641 may represent a portion of a case (e.g., case 410) that may be mounted to a wall, ceiling, or other surface. Hazard detector 600E also includes a back plate 642 that may be mounted to the mounting plate 641 and a front casing 643 that may be coupled with or otherwise secured to back plate 642 to define a housing having an interior region within which components of the hazard detector 600E are contained. A circuit board 644 may be coupled with or attached to back plate 642. Various components may be mounted on circuit board 644. For example, a smoke chamber 645 may be coupled with or mounted on circuit board 644 and may be used to detect the presence of smoke. In one embodiment, smoke chamber 645 may be mid-mounted relative to circuit board 644 so that air may flow into smoke chamber 645 from a position above circuit board 644 and below circuit board 644. A speaker 646 and alarm device (not numbered) may also be mounted on circuit board 644 to audibly warn an occupant of a potential fire danger when the presence of smoke is detected via smoke chamber 645. Other components, such as a motion sensor (e.g., PIR sensor), carbon monoxide sensor, microprocessor, and the like may likewise be mounted on circuit board 644.

In one embodiment, a protective plate 647 may be attached to or otherwise coupled with circuit board 644 to provide a visually pleasing appearance to the inner components of hazard detector 600E and/or to a funnel or a direct airflow to smoke chamber 645. For example, when a user views the internal components of hazard detector 600E, such as through vents in back plate 642, protective plate 647 may provide the appearance of a relatively smooth surface and otherwise hide the components or circuitry of circuit board 644. Protective plate 647 may likewise function to direct a flow of air from the vents of back plate 642 toward smoke chamber 645 so as to facilitate air flow into and out of smoke chamber 645.

Hazard detector 600E may also include a battery pack 648 that can provide power to the various components of hazard detector 600E such as when hazard detector 600E is not coupled with an external power source, such as an AC power source of the home or structure. In some embodiments, a cover plate 649 may be coupled with the front casing 643 to provide a visually pleasing appearance to hazard detector 600E and/or for other functional purposes. In a specific embodiment, cover plate 649 may include a plurality of holes or openings that allows one or more sensors coupled with circuit board 644 to view or see through a surface of cover plate 649 so as to sense objects external to hazard detector 600E. The plurality of openings of cover plate 649 may be arranged to provide a visually pleasing appearance when viewed by occupants of the home or structure. In one embodiment, the plurality of openings of cover plate 649 may be arranged according to a repeating pattern, such as a Fibonacci or other sequence.

A lens button 650 may be coupled with or otherwise mounted to cover plate 649. Lens button 650 may represent an embodiment of lens button 600 of FIGS. 6A and 6B. Lens button 650 may allow one or more sensors to view through the lens button 650 for various purposes. For example, in one embodiment a PIR sensor (not shown) may be positioned behind the lens button 650 and configured to view through the lens button 650 to detect the presence of an occupant or occupants within the home or structure. In some embodiments, lens button 650 may also function as a button that is pressable by a user to input various commands to hazard detector 600E, such as to shut off an alarm that is triggered in response to a false or otherwise harmless condition. Positioned distally behind lens button 650 may be a light ring 651 that receives light. Light ring 651 may represent an embodiment of light ring 620 of FIGS. 6C and 6D. Light ring 651 may receive light from at least one lighting element, such as from an LED or another light emitting element, and disperse the light within light ring 651 to provide a desired visual appearance, such as a halo around lens button 650. Positioned distally behind light ring 651 may be a flexible circuit board 652 that includes one or more electrical components, such as a PIR sensor, LEDs, and the like. As such, the PIR sensor and/or lighting elements may be located within hazard detector 600E behind lens button 650. Flexible circuit board 652 may be electrically coupled with circuit board 644 to communicate and/or receive instructions from one or more microprocessors mounted on a circuit board (not shown) during operation of hazard detector 600E.

Figure 6F:
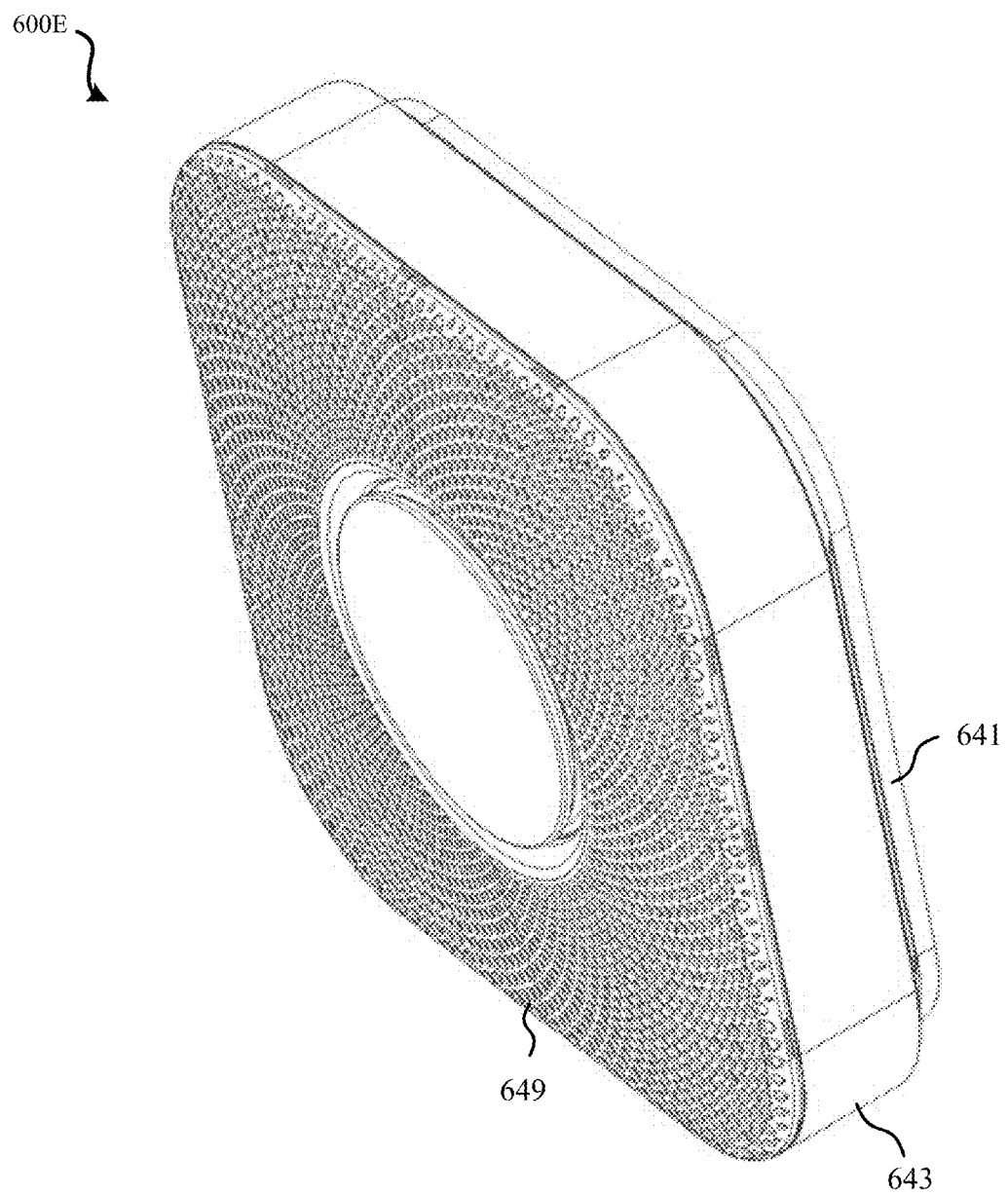
FIG. 6F illustrates a perspective view of an embodiment of a hazard detector that includes a ring-shaped light.

FIG. 6F illustrates hazard detector 600E of FIG. 6E with its various components assembled. Specifically, FIG. 6F shows the mounting plate 641, front casing 643, back plate 642, and cover plate 649 in an assembled configuration with the various other components contained within an interior space of hazard detector 600E. This figure also shows the plurality of holes or openings of cover plate 649 forming a visually pleasing design that is viewable by an occupant of a room within which the hazard detector 600E is mounted. The lens button 650 is shown attached to the hazard detector 600E so as to be centrally positioned with respect to cover plate 649.

Figure 7:
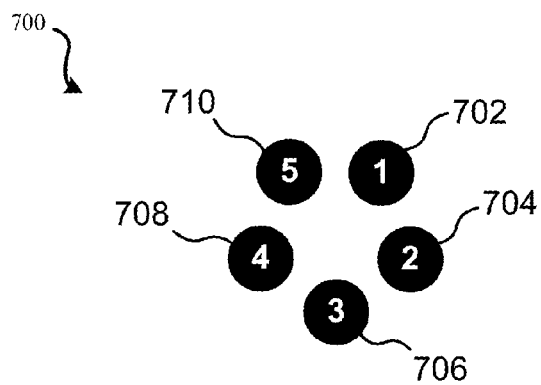
FIG. 7 illustrates an embodiment of a hazard detector having LEDs arranged in a circle.

FIG. 7 illustrates an embodiment of lighting elements 700 arranged approximately in a circle. Such a pattern of lighting elements (e.g., LED lights) may be coupled on a circumferentially arranged ring portion of a hazard detector. For instance, lighting elements 700 may be placed proximate to light ring 340 or light ring 651 such that light from lighting elements 700 is diffused in a circular pattern. Five lighting elements may be present: lighting elements 702, 704, 706, 708 and 710. Lighting elements 700 may be turned on and off according to a number of patterns (e.g., via adjustment of brightness of each lighting element) and/or each may cycle through different hue ranges (thereby changing in color). The color of each of the lighting elements may vary in order to provide an additional variety of visual effects. While five lighting elements are illustrated, it should be understood that a fewer or a greater number of lighting elements may be incorporated as part of a light of a hazard detector or some other form of device.

Figure 8A:
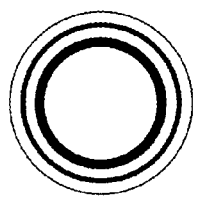
FIGS. 8A-8D illustrate an embodiment of four various visual effects that may be generated using a light of a hazard detector.

FIGS. 8A-8D illustrate an embodiment of four visual effects (also referred to as animations) that may be generated using a light of a hazard detector, such as the lights and hazard detectors detailed herein. FIG. 8A illustrates a representation of a pulsing effect that may be created when all of lighting elements 702, 704, 706, 708 and 710 (shown in FIG. 7) are turned on and off simultaneously. Alternatively, all of lighting elements 702, 704, 706, 708 and 710 may increase and decrease the brightness of the light they each produce in a synchronized fashion to create a pulsing effect. For example, for a first second (or other period of time), the brightness of each of the lighting elements may be gradually increased; for a second (or other period of time), the brightness of each of the lighting elements may be maintained constant; and, for a third second (or other period of time), the brightness of each of the lighting elements may be gradually decreased, such as to a fully off state. Table 1 represents characteristics of an exemplary embodiment of a pulsing effect.

turning on at one end of the rotating visual effect and other lights gradually turning off at the other end of the rotation visual effect. The hatch patterns of each of the sequential representations illustrate how the rotating light may change color during the rotation sequence. Although lighting elements 702, 704, 706, 708 and 710 may each be a different color individually, the colored light mixing causes the color of the rotating visual effect to constantly change through the course of the visual effect. Table 2 represents characteristics of an exemplary embodiment of a rotating effect.

TABLE 2

|  | Normal/Default | Slow |
|---|---|---|
| LE sequence | Clockwise |  |
| Start | LE 702 |  |
| LE ramp on | 400 ms | 800 ms |
| LE hold on | 0 ms | 0 ms |
| LE ramp off | 400 ms | 800 ms |
| LE hold off | 200 ms | 400 ms |
| LE fire offset | 200 ms | 400 ms |
| Cycle length | 1.2 s | 2.4 s |
| Easing | Polyline Easing Curve | Polyline Easing Curve |
| End | Fade out | Fade out |

Such an animation may be repeated a number of times or while a state of the hazard detector is active. While such an effect may be created by lighting elements 702, 704, 706, 708 and 710 of FIG. 7, it should be understood that a similar effect may be created using a greater or fewer number of lighting elements, such as by the large number of lighting elements present in FIGS. 5A and 5B.

Figure 8B:
Figure 8C:

FIG. 8C illustrates a representation of a wave visual effect that may be created when lighting elements 700 (shown in FIG. 7) turn on and off in a side-to-side direction. For

TABLE 1

|  | Normal/Default | Slow | Fast | Alarm |
|---|---|---|---|---|
| LE sequence | N/A | N/A | N/A | N/A |
| Start | Simultaneous | Simultaneous | Simultaneous | Simultaneous |
| LE ramp on | 500 ms | 1 s | 250 ms | 100 ms |
| LE hold on | 500 ms | 1 s | 250 ms | 200 ms |
| LE ramp off | 500 ms | 1 s | 250 ms | 100 ms |
| LE hold off | 1.5 s | 3 s | 750 ms | 100 ms |
| LE fire offset | N/A | N/A | N/A | N/A |
| Cycle length | 3 s | 6 s | 1.5 s | 0.5 s |
| Easing | Polyline Easing Curve | Polyline Easing Curve | Polyline Easing Curve | Polyline Easing Curve |
| End | Stop after x cycles | Stop after x cycles | Stop after x cycles | Stop after x cycles |

This pattern may repeat for a defined number of cycles. While such an effect may be created by lighting elements 702, 704, 706, 708 and 710 of FIG. 7, it should be understood that a similar effect may be created using a greater or fewer number of lighting elements.

Figure 10:
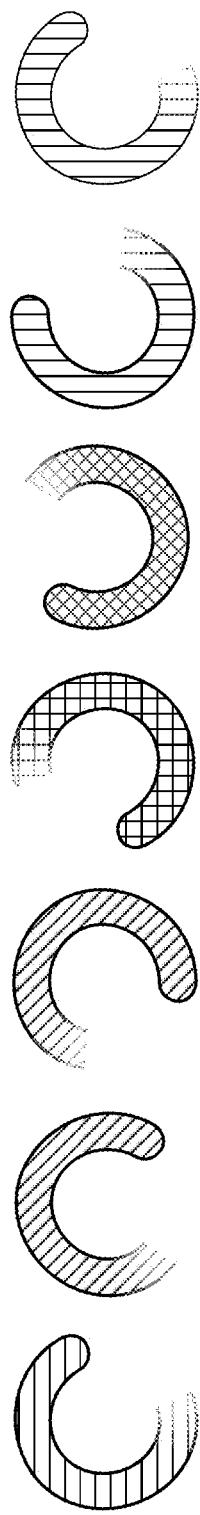
FIG. 10 illustrates another embodiment of a rotating visual effect that may be output by a hazard detector.

FIG. 8B illustrates a representation of a rotating effect (also referred to as a circulation effect or halo sweep effect) that may be created when all of lighting elements 702, 704, 706, 708 and 710 are turned on and off sequentially in a clockwise direction to create a rotating effect. Furthermore, turning on and off the lights may be done in a gradual fashion. For example, lighting element 704 may gradually turn off and lighting element 702 gradually turns on while lighting elements 706, 708 and 710 are turned on at an equal brightness. FIG. 10 provides a further illustration of the rotating visual effect of FIG. 8B (and FIGS. 5A and 5B), according to various embodiments. Viewed from left to right, FIG. 10 illustrates an effect caused by light elements example, at a given point in time as shown in FIG. 8C, lighting element 710 may be most bright, lighting elements 708 and 702 may be the next brightest, and lighting elements 706 and 704 may be the least bright. Shortly thereafter, the lights may gradually change brightness in a linear manner such that lighting elements 704 and 706 are the brightest, lighting elements 708 and 702 are the next brightest, and lighting element 710 is the least bright. Table 3 represents characteristics of an exemplary embodiment of a wave effect.

TABLE 3

|  | Normal/Default |
|---|---|
| LE sequence | 708, 710/706, 702/704 |
| Start | 708 |
| LE ramp on | 500 ms |

TABLE 3-continued

| | Normal/Default |
|---|---|
| LE hold on | 0 ms |
| LE ramp off | 500 ms |
| LE hold off | N/A |
| LE fire offset | 300 ms |
| Cycle length | 1.6 s |
| Easing | Polyline Easing Curve |
| End | One cycle |

The pattern may then be reversed and/or repeated. While such an effect may be created by lighting elements 702, 704, 706, 708 and 710 of FIG. 7, it should be understood that a similar effect may be created using a greater or fewer number of lighting elements. While only a "normal/default" speed is listed, by adjusting the times listed, different speed variations of the animation may be created.

Figure 8D:
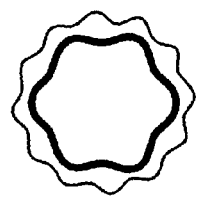
Figure 11:
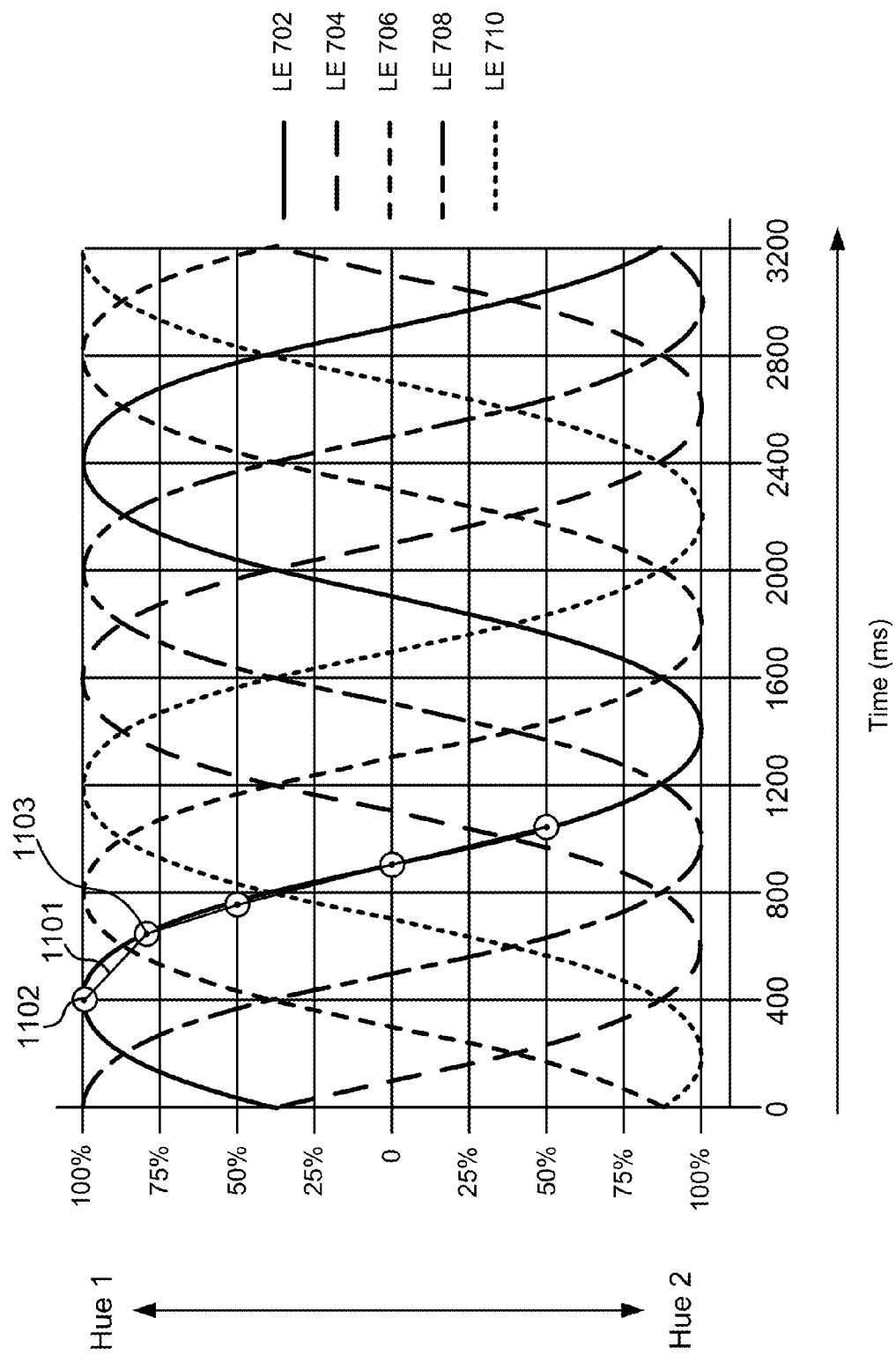
FIG. 11 illustrates an embodiment of various hue range patterns which may be used to generate visual effects by a hazard detector.

FIG. 8D illustrates a representation of a shimmer visual effect that may be created when each of the lighting elements 700 cycle through a hue range pattern with each lighting element's hue range pattern being out of sync with one or more (e.g., all) other lighting elements. FIG. 11 illustrates the different hue range patterns associated with each of the lighting elements 700 for the shimmering visual effect, according to an embodiment. While FIG. 11 shows each lighting element being out of synchronization from each other lighting element, in some embodiments, two or more of the lighting elements may be in synchronization with each other. The extent to which the lighting elements 702, 704, 706, 708 and 710 are out of sync may be varied in order to produce variations of the shimmer visual effect. Table 4 represents characteristics of an exemplary embodiment of a shimmer effect.

TABLE 4

| | Normal/Default |
|---|---|
| LE sequence | See FIG. 11 for hue curves |
| Start | Simultaneously |
| LE ramp on | 1 s |
| LE hold on | N/A |
| LE ramp off | 1 s |
| LE hold off | N/A |
| LE fire offset | See FIG. 11 |
| Cycle length | Indefinite |
| Easing | Polyline Easing Curve |
| End | Ramp off when ready to end |

While such an effect may be created by lighting elements 702, 704, 706, 708 and 710 of FIG. 7, it should be understood that a similar effect may be created using a greater or fewer number of lighting elements. While only a "normal/default" speed is listed, by adjusting the times listed, different speed variations of the animation may be created.

Figure 9A:
FIGS. 9A and 9B illustrate an embodiment of a pulse visual effect that may be generated using a light of a hazard detector.
Figure 9B:

FIGS. 9A and 9B illustrate an embodiment of a pulse visual effect that may be generated using a light of a hazard detector. FIG. 9A represents an on and off pattern wherein pulse animations will transition smoothly from off to on, then on to off, through pulses in order to provide an alert in a non-distracting manner. FIG. 9B represents left-to-right pulse patterns that could be used when presenting a user with selectable options via visual effects. For example, a user input component or, more specifically, a lens button, may be used to select a language (or other form of) preference for the operation of a hazard detector during a setup procedure. A user could be asked to press such a lens button when the left side is pulsing for English (or, more generally, a first option) and when the right side is pulsing for Chinese (or, more generally, a second option). Therefore, a user may wait until the side of light is pulsing or otherwise illuminated that is associated with the user's desired selection. Similarly, different colors may be associated with different options available for selection: a user may wait until a color is output that corresponds to the user's desired selection. In some embodiments, rather than pressing a button, the user may perform a gesture, such as one or multiple waves of a hand.

In various embodiments, the visual effects described above could be varied in a number of different ways. For example, each effect may be animated faster or slower, brighter or dimmer, for a specific number of animation cycles, with only some of the light participating, and using different colors, e.g., white, blue, green, yellow and red, and/or a mixture of multiple colors.

These visual effects may be generated by the hazard detectors detailed herein for a variety of specified purposes. For example, a specific color, animation, animation speed, etc. or combinations thereof may represent one or more of the following alerts or notifications provided a hazard detector: booting up, selecting language, ready for connections, connected to client, button pressed, button pressed for test, countdown to test, test under way, test completed, pre-alarms, smoke alarms, carbon monoxide alarms, heat alarms, multi-criteria alarms, hushed after alarm, post-alarm, problems, night light state, reset, shutdown begin, shutdown, safely light, battery very low, battery critical, power confirmation, and more. By way of example and not by way of limitation, FIGS. 12 and 13 illustrate an exemplary "visual vocabulary" for visual effects and colors that may be used by embodiments of hazard detectors.

FIG. 11 illustrates various hue range patterns associated with each of the lighting elements 700 for the shimmering visual effect, according to an embodiment. The extent to which lighting elements (abbreviated LE in FIGS. 11) 702, 704, 706, 708 and 710 are out of sync may be varied in order to produce variations of the shimmer visual effect. As illustrated, each lighting element is increased and decreased in brightness between two hues as time progresses. Some or all of the lighting elements are "out of sync" in that the lighting elements, while illuminating according to the same pattern, do so at different times. While two hues may be used, it should be understood that a single hue may be possible (e.g., fading between a first hue and off) or more than two hues (e.g., per lighting element or using different color pairs for different lighting elements of the light). While such an effect may be created by lighting elements 702, 704, 706, 708 and 710 of FIG. 7, it should be understood that a similar effect may be created using a greater or fewer number of lighting elements. Also, the waveforms could be altered to produce a different visual effect.

In FIG. 11, sine waves are used to define the adjustment between hue intensity levels of individual lighting elements for a shimmer visual effect. In some embodiments, multiple linear transitions stored by a hazard detector and may be used to approximate such curves. Such an implementation may be referred to as polyline easing and may require less processing for the hazard detector to implement. As an example, a portion of polyline easing, the hue transition for LE 702 has been represented using multiple linear segments defined by transition points (e.g., transition point 1102 and transition point 1103, which each have an associated set of coordinates). Line segments 1101 represent such polyline easing, which is defined based on reference points including reference points 1102 and 1103. Such transitions may be defined for all lighting elements and/or all lighting effects detailed herein.

FIG. 12A illustrates an embodiment 1200A of definitions for visual effects that may be used by a hazard detector, such as the hazard detectors detailed herein. Color definitions 1210, animation definitions 1220, and speed definitions 1230 may be stored locally by a hazard detector (e.g., stored as part of stored illumination definitions 243) or may be accessible by the hazard detector from some remote location, such as from cloud-based server (e.g., a cloud-computing system). Such definitions of colors, animations, and/or speeds may be provided to a user, such as in the form of a quick reference sheet or manual provided with a hazard detector when purchased. As such, a user can learn or look-up the meaning of a particular visual effect. Each color, animation, and speed may have an individualized meaning. For instance, the speed of an animation may be used to indicate a level of urgency. Animation may be used to provide an acknowledgment ("OK"), an indication that attention is needed, and/or some other status. Such an animation used in conjunction with a speed may alert the user as to how urgent the status associated with the animation is. Further, various colors may be incorporated to provide more information to a user, such as green for "OK", yellow for "something may be wrong" or a warning, and red for "something is definitely wrong." Other colors may be used for other forms of messages. Further, a separate color, such as white, may be used by the light for ambient lighting provided by the hazard detector in certain situations as previously detailed. As an example, if a battery is low but does not yet need to be replaced, the color may be yellow ("something may be wrong"), the animation may be "here's my status", and the speed may be slow. If the battery is not replaced, the speed may transition to fast after a time. Once the battery must be replaced, the color may be red ("something is definitely wrong"), the animation may be a circulation ("I need your attention") and the speed may be fast (or alarm). As such, a battery may be checked against multiple voltage thresholds—the lower the voltage, the more urgent the presented status.

In some embodiments, color definitions 1210, animation definitions 1220, and speed definitions 1230 may be used independently to select a color, animation, and speed by the hazard detector based on a status check of the hazard detector. A look-up may be performed using color definitions 1210, animation definitions 1220, and speed definitions 1230 to select a color, animation, and speed that correspond to the status determined by the hazard detector. The color, animation, and/or speed selected from color definitions 1210, animation definitions 1220, and/or speed definitions 1230 may then be used by the hazard detector to output a status via a light of the hazard detector.

FIG. 12B illustrates an embodiment 1200B of various combinations of visual effects (also referred to as animations) and color that may be used by a hazard detector, such as the hazard detectors detailed herein. Such combinations may be stored in the form of a look-up table by a hazard detector or may be accessible via a network from a remote computerized device, such as a cloud-based server system (e.g., cloud-computing system 1564). Once a status is determined by the hazard detector, a table such as presented in embodiment 1200B may be used to determine an animation, color, speed, and/or duration to use for outputting an indication of the status. Color 1251 may be red, color 1252 may be yellow, color 1253 may be green, color 1254 may be blue, and color 1255 may be white. Other color assignments are also possible. Definitions of colors, visual effects, and/or speeds may be stored by a hazard detector, such as in stored illumination definitions 243, which may be present on a non-transitory processor-readable medium. In response to a condition determined by the hazard detector (e.g., by state determination engine 241), the processing system of the hazard detector may look up or otherwise determine (e.g., using definition lookup and output engine 242) the appropriate combination of colors, visual effect, and/or speed to use to illuminate the light. The light may then be illuminated according to the determined combination to convey information to one or more users. Again here, definitions of colors and animations may be provided to a user, such as in the form of a quick reference sheet or manual provided with a hazard detector when purchased.

FIGS. 13A-13D represent various lighting effects of how a hazard detector may be illuminated to communicate information to a user. Category 1301 may represent the category of a type of function. Name 1302 may represent the name of the function being performed by the hazard detector. Type 1303 may indicate whether the corresponding function is a state or event. An event may be a discrete event, such as a button push, while a state may be an on-going condition, such as an alarm being active. LED behavior 1304 may represent the various behaviors of LEDs of the hazard detector's light, such as an animation, color, timing (e.g., once, three times, for x amount of time, until an event occurs, while a state is present), and a speed variation (e.g., normal, fast, slow, alarm speed, etc.). Tone 1305 may represent a sound that is output by the hazard detector to accompany the lighting effect. Voice 1306 may represent a recorded or synthesized spoken message to accompany the lighting effect. Such lighting effects may be stored in the form of a look-up table by a hazard detector or may be accessible via a network from a remote computerized device, such as a cloud-based server system (e.g., cloud-computing system 1564). Once a status is determined by the hazard detector, a table such as presented in embodiments 1300A through 1300D may be used to determine an animation, color, speed, and/or duration to use for outputting an indication of the status.

Figure 14A:
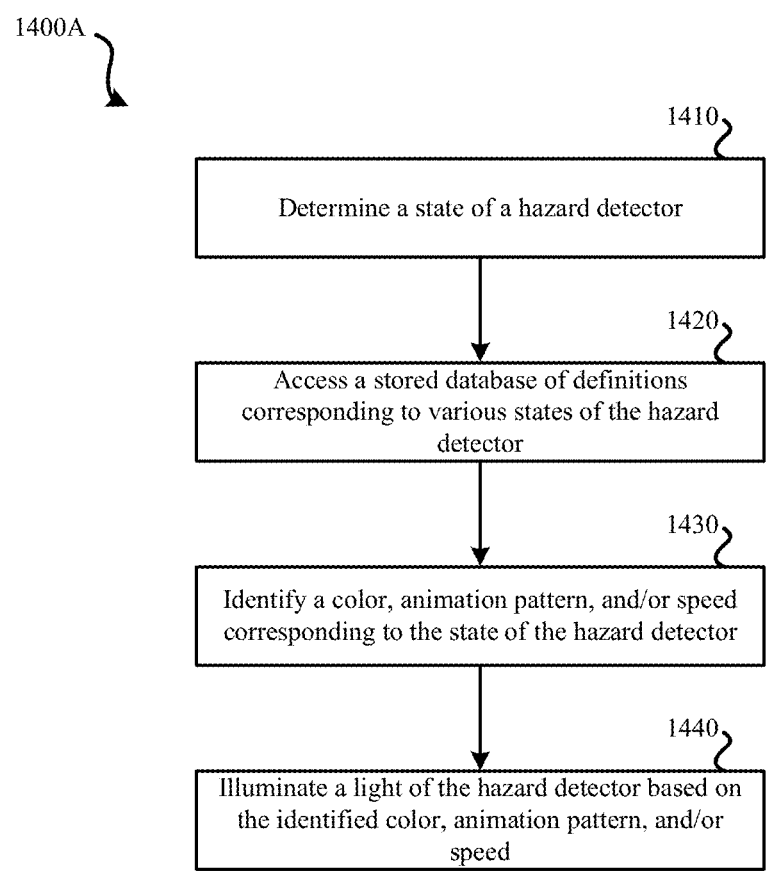
FIG. 14A illustrates an embodiment of a method for presenting information via a ring-shaped light of a hazard detector.

The embodiments of hazard detectors detailed herein may be used to perform various methods. FIG. 14A illustrates an embodiment of a method 1400A for presenting information via a ring-shaped light of a hazard detector. Method 1400A may be performed using the hazard detectors, related components, and animation patterns detailed in relation to FIGS. 1-13.

At block 1410, a state of the hazard detector may be determined. The state may be determined by the hazard detector performing a status check of itself or an alarm being triggered. The state may be determined based on the status of one or more hazard sensors, such as a smoke sensor and/or a carbon monoxide sensor, present on the hazard detector. The state of the hazard detector may also be based on a charge level of an onboard battery. State of the hazard detector may also be based upon a status of a user account that is tied to the hazard detector and is maintained by a remote server system. Such states may also be understood to include events. For example, an event may be a button press or a network being detected. Therefore, a state of the hazard detector being determined may include an event occurring at the hazard detector being determined. Block 1410 may be performed by an onboard processing system of hazard detector. For example, referring to hazard detector 200, state determination engine 241 of processing system 110 may determine a state of the hazard detector.

At block 1420, a stored database, table, or other storage arrangement of illumination definitions corresponding to various states of the hazard detector may be accessed. The stored illumination definitions may be stored locally by the hazard detector and/or may be accessible via a network connection from a remote computer system, such as the computer system that maintains the user account that may be associated with the hazard detector. The stored database may include information such as that presented in FIGS. 12 and 13. As such, these stored database of definitions may include indications of color, animation, and/or speed that are associated with states of the hazard detector. Referring to hazard detector 200, definition lookup and output engine 242 of processing system 110 may be configured to access the stored illumination definitions 243. While hazard detector 200 illustrates stored illumination definitions 243 are stored locally using a non-transitory processor-readable medium at the hazard detector, it should be understood that stored illumination definitions 243 may be stored remotely from the hazard detector may be accessible via wireless communication module 230. It should be understood that the processing system of the hazard detector may be configured to periodically update its stored illumination definitions with a remote server when an update is available to such definitions from a remote server. For instance, when the hazard detector checks on a condition of the user account associated with the hazard detector, the hazard detector may be notified that its stored illumination definitions are to be updated.

At block 1430, the appropriate color (or the appropriate multiple colors), animation pattern, and/or speed may be determined by the hazard detector by accessing the stored illumination definitions. The color, animation pattern, and/or speed may be associated with the state of the hazard detector determined at block 1410. Therefore, based on the determined state of the hazard detector, the hazard detector can determine an appropriate one or more colors, one or more animations, and/or speed for the animation for use in illuminating a light to provide a user with information about the state. Referring to hazard detector 200, block 1430 may involve the one or more colors, animations, and/or speeds being retrieved by definition lookup and output engine 242 from stored illumination definitions 243.

At block 1440, the light of the hazard detector may be illuminated based on the identified one or more colors, animation pattern, and/or speed. Illumination of the light may include one or more lighting elements of the light being simultaneously or intermittently illuminated, such as to cause output of any of the various animation patterns previously detailed. Further, the color output by the light of the hazard detector may be constant or may vary. Further, the speed of an animation, such as the speed of the circulating effect, may be varied to provide a user with different information. Depending on the state determined at block 1410, the amount of time for which the light is illuminated may vary. For example, if the state of the hazard detector is indicative of a fire, the light may be illuminated until smoke from the fires no longer detected. As another example, if the state of the hazard detector is indicative of a low battery, the light of the hazard detector may illuminate for three seconds.

Figure 14B:
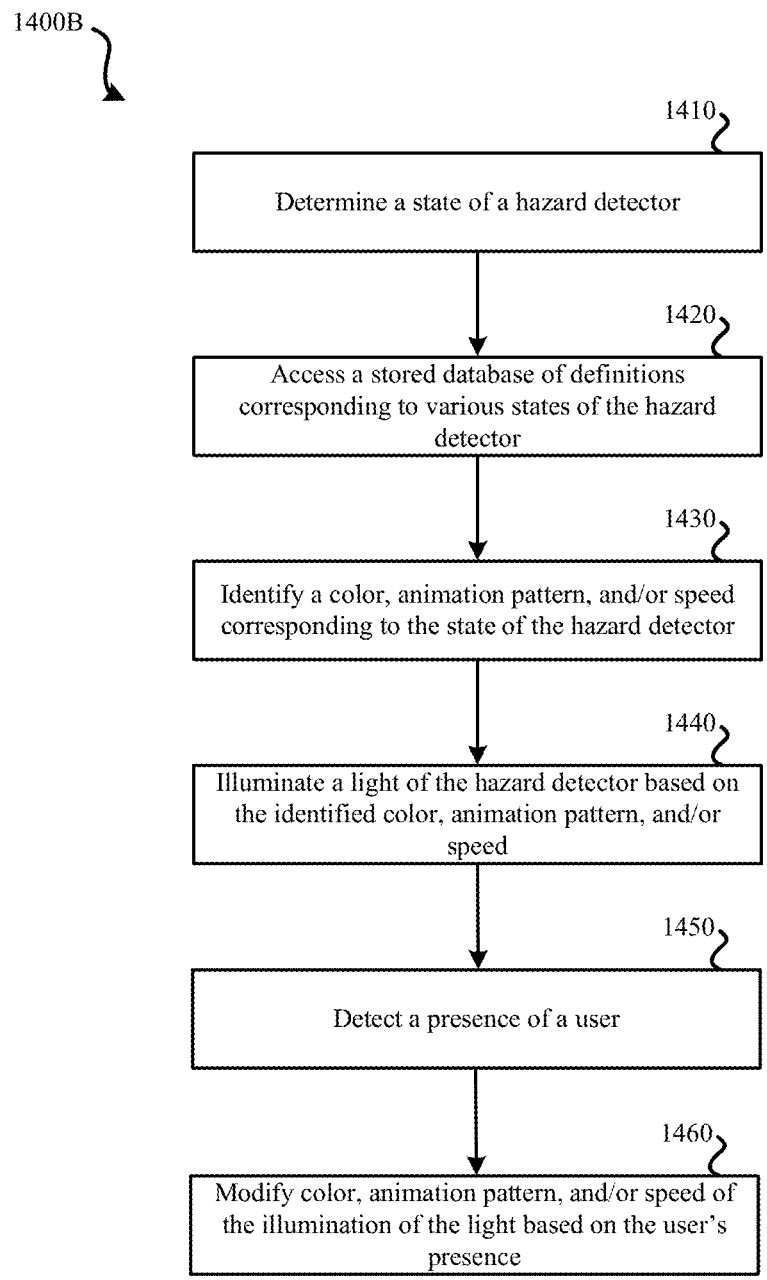
FIG. 14B illustrates another embodiment of a method for presenting information via a ring-shaped light of a hazard detector.

FIG. 14B illustrates another embodiment of a method 1400B for presenting information via a ring-shaped light of a hazard detector. Method 1400B may represent an alternate embodiment of method 1400A. Blocks 1410 through 1440 may be performed similarly to as described in relation to FIG. 14A. At step 1450, a user's presence in the ambient environment of the hazard detector may be detected. For instance, a PIR sensor and/or ultrasonic sensor of the hazard detector may sense a user's presence, such as based on received infrared radiation and/or detected motion, respectively.

In response to a user's presence being detected, the color, animation, and/or speed at which the light of the hazard detector is being illuminated may be changed by the hazard detector at block 1460. This modification of the color, animation, and/or speed used to illuminate the light may alert the user as to whether his presence is detected by the hazard detector. By the user knowing that his presence has been detected, the user may expect that any provided input, such as a gesture or voice command, will be received by the hazard detector. In some embodiments, the modification to the color, animation, and/or speed used to illuminate the light includes ceasing any animation and illuminating the light in a solid pattern. For instance, a circulation effect may be stopped and the light may be illuminated at a constant brightness in response to the presence of a user being detected. If the user moves away and is no longer detected, the animation may resume. In other embodiments, color and/or speed may be modified in response to a user presence being detected.

Figure 14C:
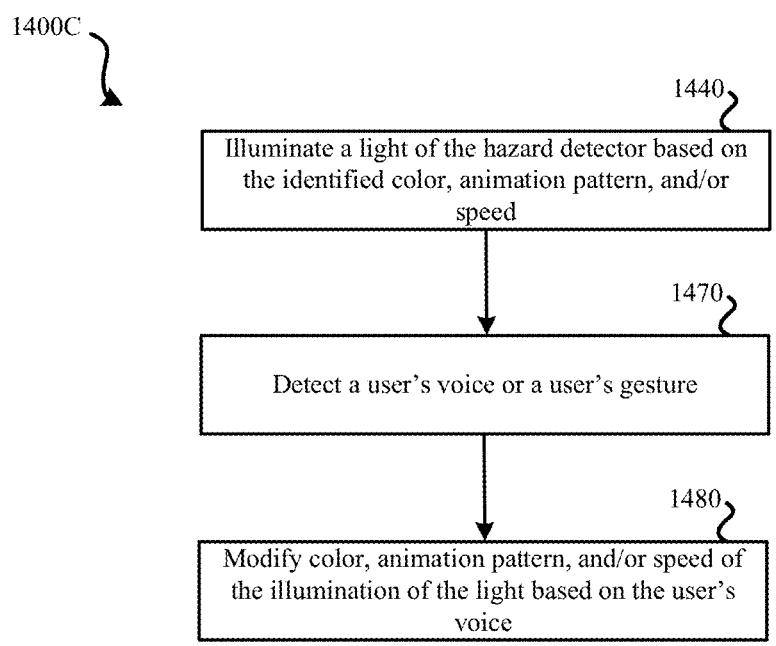
FIG. 14C illustrates an embodiment of a method for modifying the information presented via a ring-shaped light of a hazard detector based on a user's voice.

FIG. 14C illustrates an embodiment of a method 1400C for modifying the information presented via a ring-shaped light of a hazard detector based on a user's voice. Method 1400C may represent an alternate embodiment of method 1400A and/or method 1400B. Blocks 1410 through 1430 may also be performed, as described in relation to FIG. 14A, as part of method 1400C. Block 1440 may be performed as previously detailed in relation to method 1400A.

At block 1470, a user's voice may be detected, such as via a microphone of the hazard detector. For example, the user may say: "Silence the alarm!" At block 1470, a microphone may receive audio spoken by a user. Data corresponding to such audio may be transmitted by the microphone to the processing system of the hazard detector for analysis. Additionally or alternatively, a gesture being performed by the user may be detected by the hazard detector, such as via a PIR sensor or an ultrasonic sensor. For example, the user may perform a gesture that includes multiple waves.

At block 1480, in response to detecting the user's voice (and/or the gesture), the brightness, color, animation, and/or speed of the illumination of the light may be modified. For instance, the brightness of the light may be modulated according to the detected volume or inflection of the user's detected voice. Such modulation of the brightness may alert the user that the hazard detector is receiving and processing the user's voice. The captured audio from the user may be analyzed to detect a command to be executed by the hazard detector. In some embodiments, the animation of the hazard detector is ceased in response to the user's voice being detected. For instance, a circulation animation may stop and the light may illuminate a constant brightness while the user is speaking. In some embodiments, method 1400B may be performed in conjunction with method 1400C: The color, animation, and/or speed of the light may be modified in response to the user's presence being detected then, in response to the user's voice being detected, the output light may be modulated based on the volume and/or inflection of the user's voice. If a gesture is detected at block 1470, the illumination of the light may be varied in response to the user's gesture to provide the user with an indication that the gesture has been detected. For instance, if a user performs a wave gesture, the wave animation of FIG. 8C may be performed to echo back to the user that the wave gesture has been received. The mimicked animation based on the gesture may match the directionality and/or speed of the user's gesture. For instance, a wave left followed by a wave right by a user may result in the hazard detector outputting the wave animation to the left then to the right.

Figure 15:
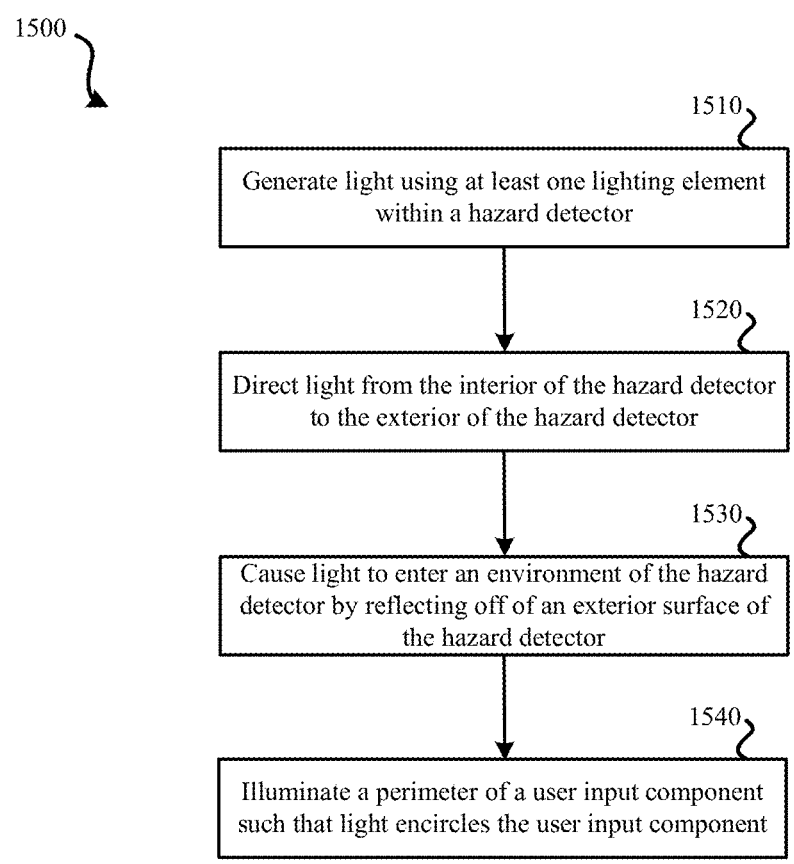
FIG. 15 illustrates an embodiment of a method for using a ring-shaped light to emit light from a hazard detector.

FIG. 15 illustrates an embodiment of a method 1500 using a ring-shaped light to emit light from a hazard detector. While method 1500 focuses on the use of a ring-shaped light, it should be understood that method 1500 can be applied to a light that is in the form of some other shape. Method 1500 may be performed in conjunction with one or more other methods, such as method 1400 of FIG. 14. Further, method 1500 may be performed by the hazard detectors detailed in this document.

At block 1510, the light of a hazard detector may generate light. Generation of light may occur via one or more lighting elements of the light. For example, in some embodiments, a light can have multiple LEDs that generate light at a same or different brightness level and/or a same or different color. At block 1520, light from the lighting elements may be directed from the interior of the hazard detector to the exterior of the hazard detector. As such, the lighting elements may not be directly visible by user that is external to the hazard detector. To direct light at block 1520, a light ring or other form of guide may be used to direct the light from the lighting elements to the exterior of the hazard detector. For example, referring to FIGS. 6C and 6D, light ring 620 may be used to direct light from multiple LEDs to an exterior of the hazard detector. Such a light ring may be partially or fully hidden within the hazard detector. For example, light ring 620 may be located behind a user interface (e.g., button) such that light ring 620 is not directly visible to a user (or is at least hard to see). Such a light ring or other form of guide may disperse light generated by the lighting elements. Such disbursement of the light may allow multiple point sources of light, such as LEDs, which are being used as the lighting elements to illuminate a shape continuously. Therefore, one or more lighting elements may be used to produce a ring or other shape of output light.

At block 1530, at least some light generated by the lighting elements may enter the external environment of the hazard detector by reflecting off an external surface of the hazard detector. Such lighting may be referred to as indirect lighting. For example, in exterior portion of the hazard detector that is configured to face in the direction of the user may have a recessed portion that reflects light that is received either from the lighting elements directly or as directed by the light ring or other form of guide. For example, referring to FIG. 6E, light directed by light ring 651 may be configured to reflect into the exterior environment of hazard detector 600E off a recessed portion of cover plate 649 (which is part of a case of hazard detector 600E). In other embodiments, light from the lighting elements may enter the external environment directly from the lighting elements or the light ring. That is, light reflecting, if any, off of the case of the hazard detector may be incidental.

At block 1540, the light entering the environment of the hazard detector may illuminate an edge of the user input component such that light encircles or otherwise outlines the user input component. Therefore, by user pressing or touching within the illuminated circle or other shape, the user can assume he is touching the user input component. Such an arrangement may be particularly useful in a darkened environment. A sensor, such as a PIR sensor, may be located within the hazard detector behind the user input component. By performing a gesture or otherwise being present proximate to the shape defined by the light, the user may determine that he is in the proper location to perform the gesture or be sensed. It is to be appreciated that while the described methods and systems for intuitive illumination-based status signaling for a hazard detector are particularly advantageous in view of the particular device context, in that issues may be brought about by the lack of a full on-device graphical user interface (e.g., the lack of a dot-matrix LCD screen with touchscreen capability or keypad/pointer capability) with the use instead of non-graphical but simple, visually appealing on-device user interface elements (e.g., a simple pressable button with shaped on-device lighting), and in further view of power limitations for the case of battery-only hazard detectors making it desirable for status communications using minimal amounts of electrical power, the scope of the present disclosure is not so limited. Rather, the described methods and systems for intuitive illumination-based status signaling are widely applicable to any of a variety of smart-home devices such as those described in relation to FIG. 16 infra and including, but not limited to, thermostats, environmental sensors, motion sensors, occupancy sensors, baby monitors, remote controllers, key fob remote controllers, smart-home hubs, security keypads, biometric access controllers, other security devices, cameras, microphones, speakers, time-of-flight based LED position/motion sensing arrays, doorbells, intercom devices, smart light switches, smart door locks, door sensors, window sensors, generic programmable wireless control buttons, lighting equipment including night lights and mood lighting, smart appliances, entertainment devices, home service robots, garage door openers, door openers, window shade controllers, other mechanical actuation devices, solar power arrays, outdoor pathway lighting, irrigation equipment, lawn care equipment, or other smart home devices. Although widely applicable for any of such smart-home devices, one or more of the described methods and systems become increasingly advantageous when applied in the context of devices that may have more limited on-device user interface capability (e.g., without graphical user interfaces) and/or having power limitations that make it desirable for status communications using minimal amounts of electrical power. According to one embodiment, the user can be provided with a suite of related smart-home devices, such as may be provided by a common manufacturer or group or badged to work with a common "ecosystem" of that manufacturer or group, wherein each of the devices, where practicable, provides a same or similar illumination-based notification scheme and theme, such that the user can be readily familiar with the status signals emitted by the variety of different devices without needing to learn a different scheme for each device. Thus, by way of example, there can be provided a suite of devices including a security/automation hub, multiple door/window sensors, and multiple hazard detectors, wherein each such device has a circular illumination ring that conveys visual information according to the themes and schemes described herein. Having read this disclosure, one having skill in the art could apply the methods and systems of the present invention in the context of one or more of the above-described smart home devices.

Figure 16:
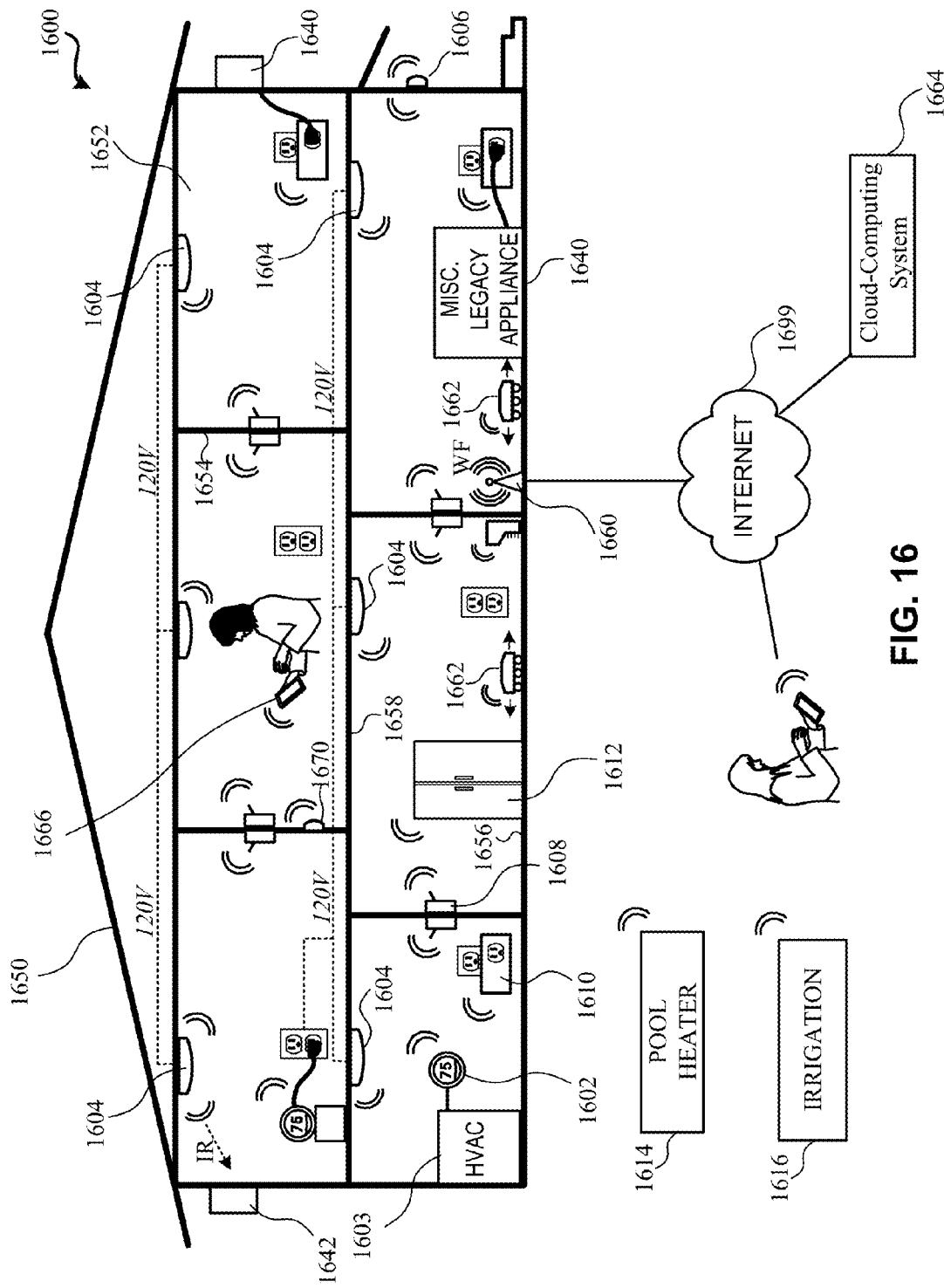
FIG. 16 illustrates an embodiment of a smart-home environment within which one or more of the devices, methods, systems, services, and/or computer program products described herein may be applicable.

Hazard detectors, as detailed herein, may be installed in a smart-home environment. FIG. 16 illustrates an example of a smart-home environment 1600 within which one or more of the devices, methods, systems, services, and/or computer program products described further herein can be applicable. The depicted smart-home environment 1600 includes a structure 1650, which can include, e.g., a house, office building, garage, or mobile home. It will be appreciated that devices can also be integrated into a smart-home environment 1600 that does not include an entire structure 1650, such as an apartment, condominium, or office space. Further, the smart home environment can control and/or be coupled to devices outside of the actual structure 1650. Indeed, several devices in the smart home environment need not physically be within the structure 1650 at all. For example, a device controlling a pool heater or irrigation system can be located outside of the structure 1650.

The depicted structure 1650 includes a plurality of rooms 1652, separated at least partly from each other via walls 1654. The walls 1654 can include interior walls or exterior walls. Each room can further include a floor 1656 and a ceiling 1658. Devices can be mounted on, integrated with and/or supported by a wall 1654, floor 1656 or ceiling 1658.

In some embodiments, the smart-home environment 1600 of FIG. 16 includes a plurality of devices, including intelligent, multi-sensing, network-connected devices, that can integrate seamlessly with each other and/or with a central server or a cloud-computing system to provide any of a variety of useful smart-home objectives. The smart-home environment 1600 may include one or more intelligent, multi-sensing, network-connected thermostats 1602 (hereinafter referred to as smart thermostats 1602), one or more intelligent, network-connected, hazard detectors 1604, and one or more intelligent, multi-sensing, network-connected entryway interface devices 1606 (hereinafter referred to as "smart doorbells 1606"). According to embodiments, the smart thermostat 1602 detects ambient climate characteristics (e.g., temperature and/or humidity) and controls a HVAC system 1603 accordingly. The hazard detector 1604 may detect the presence of a hazardous substance or a substance indicative of a hazardous substance (e.g., smoke, fire, or carbon monoxide). The smart doorbell 1606 may detect a person's approach to or departure from a location (e.g., an outer door), control doorbell functionality, announce a person's approach or departure via audio or visual means, or control settings on a security system (e.g., to activate or deactivate the security system when occupants go and come).

In some embodiments, the smart-home environment 1600 of FIG. 16 further includes one or more intelligent, multi-sensing, network-connected wall switches 1608 (hereinafter referred to as "smart wall switches 1608"), along with one or more intelligent, multi-sensing, network-connected wall plug interfaces 1610 (hereinafter referred to as "smart wall plugs 1610"). The smart wall switches 1608 may detect ambient lighting conditions, detect room-occupancy states, and control a power and/or dim state of one or more lights. In some instances, smart wall switches 1608 may also control a power state or speed of a fan, such as a ceiling fan. The smart wall plugs 1610 may detect occupancy of a room or enclosure and control supply of power to one or more wall plugs (e.g., such that power is not supplied to the plug if nobody is at home).

Still further, in some embodiments, the smart-home environment 1600 of FIG. 16 includes a plurality of intelligent, multi-sensing, network-connected appliances 1612 (hereinafter referred to as "smart appliances 1612"), such as refrigerators, stoves and/or ovens, televisions, washers, dryers, lights, stereos, intercom systems, garage-door openers, floor fans, ceiling fans, wall air conditioners, pool heaters, irrigation systems, security systems, and so forth. According to embodiments, the network-connected appliances 1612 are made compatible with the smart-home environment by cooperating with the respective manufacturers of the appliances. For example, the appliances can be space heaters, window AC units, motorized duct vents, etc. When plugged in, an appliance can announce itself to the smart-home network, such as by indicating what type of appliance it is, and it can automatically integrate with the controls of the smart-home. Such communication by the appliance to the smart home can be facilitated by any wired or wireless communication protocols known by those having ordinary skill in the art. The smart home also can include a variety of non-communicating legacy appliances 1640, such as old conventional washer/dryers, refrigerators, and the like which can be controlled, albeit coarsely (ON/OFF), by virtue of the smart wall plugs 1610. The smart-home environment 1600 can further include a variety of partially communicating legacy appliances 1642, such as infrared ("IR") controlled wall air conditioners or other IR-controlled devices, which can be controlled by IR signals provided by the hazard detectors 1604 or the smart wall switches 1608.

According to embodiments, the smart thermostats 1602, the hazard detectors 1604, the smart doorbells 1606, the smart wall switches 1608, the smart wall plugs 1610, and other devices of the smart-home environment 1600 are modular and can be incorporated into older and new houses. For example, the devices are designed around a modular platform consisting of two basic components: a head unit and a back plate, which is also referred to as a docking station. Multiple configurations of the docking station are provided so as to be compatible with any home, such as older and newer homes. However, all of the docking stations include a standard head-connection arrangement, such that any head unit can be removably attached to any docking station. Thus, in some embodiments, the docking stations are interfaces that serve as physical connections to the structure and the voltage wiring of the homes, and the interchangeable head units contain all of the sensors, processors, user interfaces, the batteries, and other functional components of the devices.

The smart-home environment 1600 may also include communication with devices outside of the physical home but within a proximate geographical range of the home. For example, the smart-home environment 1600 may include a pool heater monitor 1614 that communicates a current pool temperature to other devices within the smart-home environment 1600 or receives commands for controlling the pool temperature. Similarly, the smart-home environment 1600 may include an irrigation monitor 1616 that communicates information regarding irrigation systems within the smart-home environment 1600 and/or receives control information for controlling such irrigation systems. According to embodiments, an algorithm is provided for considering the geographic location of the smart-home environment 1600, such as based on the zip code or geographic coordinates of the home. The geographic information is then used to obtain data helpful for determining optimal times for watering; such data may include sun location information, temperature, due point, soil type of the land on which the home is located, etc.

By virtue of network connectivity, one or more of the smart-home devices of FIG. 16 can further allow a user to interact with the device even if the user is not proximate to the device. For example, a user can communicate with a device using a computer (e.g., a desktop computer, laptop computer, or tablet) or other portable electronic device (e.g., a smartphone) 1666. A webpage or app can be configured to receive communications from the user and control the device based on the communications and/or to present information about the device's operation to the user. For example, the user can view a current setpoint temperature for a device and adjust it, using a computer. The user can be in the structure during this remote communication or outside the structure.

As discussed, users can control and interact with the smart thermostat, hazard detectors 1604, and other smart devices in the smart-home environment 1600 using a network-connected computer or portable electronic device 1666. In some examples, some or all of the occupants (e.g., individuals who live in the home) can register their device 1666 with the smart-home environment 1600. Such registration can be made at a central server to authenticate the occupant and/or the device as being associated with the home and to give permission to the occupant to use the device to control the smart devices in the home. An occupant can use his registered device 1666 to remotely control the smart devices of the home, such as when the occupant is at work or on vacation. The occupant may also use his registered device to control the smart devices when the occupant is actually located inside the home, such as when the occupant is sitting on a couch inside the home. It should be appreciated that, instead of or in addition to registering devices 1666, the smart-home environment 1600 makes inferences about which individuals live in the home and are therefore occupants and which devices 1666 are associated with those individuals. As such, the smart-home environment "learns" who is an occupant and permits the devices 1666 associated with those individuals to control the smart devices of the home.

In some embodiments, in addition to containing processing and sensing capabilities, each of the devices 1602, 1604, 1606, 1608, 1610, 1612, 1614, and 1616 (collectively referred to as "the smart devices") is capable of data communications and information sharing with any other of the smart devices, as well as to any central server or cloud-computing system or any other device that is network-connected anywhere in the world. The required data communications can be carried out using one or more of a variety of custom or standard wireless protocols (cellular, 3G/4G, Wi-Fi, ZigBee, 6LoWPAN, BLE, etc.) and/or any of a variety of custom or standard wired protocols (CAT6 Ethernet, HomePlug, etc.). One particularly useful protocol that can be used is the Thread protocol, which is promulgated by the Thread Group and based on 802.15.4, IETF IPv6, and 6LoWPAN. For some embodiments, devices that are powered by the household mains current, either directly or through an AC power adapter, can be provided with a combination of Wi-Fi, which can be relatively power-intensive, along with one or more lower-power protocols such as Thread and/or BLE. In contrast, devices that are power-constrained in that they are not powered by the household mains current and do not have access to a high-capacity battery source are provided only with one or more low-power protocols such as Thread and/or BLE. In some cases, devices that are not powered by the household mains current, but do have access to a reasonably high-capacity battery source, can be provided with a combination of Wi-Fi and one or more lower-power protocols such as Thread and/or BLE, with the Wi-Fi communications being controlled to be temporally restricted, such as being turned on only during brief periodic time intervals (e.g., once per day to upload logs and receive updates from the cloud), during particular device-sensed events, or when the user has physically actuated the device such as by pressing a button on the device. The hazard detectors described herein can be provided in two different SKUs, one SKU being mains-powered with battery backup and the other SKU being battery only, albeit with a relatively large battery source (e.g., six lithium AA cells). For this battery-only SKU, the hazard detector is preferably provided with a combination of the temporally restricted Wi-Fi and one or more lower-power protocols such as Thread and/or BLE.

According to embodiments, all or some of the smart devices can serve as wireless or wired repeaters. For example, a first one of the smart devices can communicate with a second one of the smart devices via a wireless router 1660. The smart devices can further communicate with each other via a connection to a network, such as the Internet 1699. Through the Internet 1699, the smart devices can communicate with a cloud-computing system 1664, which can include one or more centralized or distributed server systems. The cloud-computing system 1664 can be associated with a manufacturer, support entity, or service provider associated with the device. For one embodiment, a user may be able to contact customer support using a device itself rather than needing to use other communication means such as a telephone or Internet-connected computer. Further, software updates can be automatically sent from cloud-computing system 1664 to devices (e.g., when available, when purchased, or at routine intervals).

According to embodiments, the smart devices combine to create a mesh network of spokesman and low-power nodes in the smart-home environment 1600, where some of the smart devices are "spokesman" nodes and others are "low-powered" nodes. Some of the smart devices in the smart-home environment 1600 are battery powered, while others have a regular and reliable power source, such as by connecting to wiring (e.g., to 120V line voltage wires) behind the walls 1654 of the smart-home environment. The smart devices that have a regular and reliable power source are referred to as "spokesman" nodes. These nodes are equipped with the capability of using any wireless protocol or manner to facilitate bidirectional communication with any of a variety of other devices in the smart-home environment 1600 as well as with the cloud-computing system 1664. On the other hand, the devices that are battery powered are referred to as "low-power" nodes. These nodes tend to be smaller than spokesman nodes and can only communicate using wireless protocols that require very little power, such as Zigbee, 6LoWPAN, etc. Further, some, but not all, low-power nodes are incapable of bidirectional communication. These low-power nodes send messages, but they are unable to "listen". Thus, other devices in the smart-home environment 1600, such as the spokesman nodes, cannot send information to these low-power nodes.

As described, the smart devices serve as low-power and spokesman nodes to create a mesh network in the smart-home environment 1600. Individual low-power nodes in the smart-home environment regularly send out messages regarding what they are sensing, and the other low-powered nodes in the smart-home environment—in addition to sending out their own messages—repeat the messages, thereby causing the messages to travel from node to node (i.e., device to device) throughout the smart-home environment 1600. The spokesman nodes in the smart-home environment 1600 are able to "drop down" to low-powered communication protocols to receive these messages, translate the messages to other communication protocols, and send the translated messages to other spokesman nodes and/or cloud-computing system 1664. Thus, the low-powered nodes using low-power communication protocols are able to send messages across the entire smart-home environment 1600 as well as over the Internet 1699 to cloud-computing system 1664. According to embodiments, the mesh network enables cloud-computing system 1664 to regularly receive data from all of the smart devices in the home, make inferences based on the data, and send commands back to one of the smart devices to accomplish some of the smart-home objectives described herein.

As described, the spokesman nodes and some of the low-powered nodes are capable of "listening." Accordingly, users, other devices, and cloud-computing system 1664 can communicate controls to the low-powered nodes. For example, a user can use the portable electronic device (e.g., a smartphone) 1666 to send commands over the Internet 1699 to cloud-computing system 1664, which then relays the commands to the spokesman nodes in the smart-home environment 1600. The spokesman nodes drop down to a low-power protocol to communicate the commands to the low-power nodes throughout the smart-home environment, as well as to other spokesman nodes that did not receive the commands directly from the cloud-computing system 1664.

An example of a low-power node is a smart nightlight 1670. In addition to housing a light source, the smart nightlight 1670 houses an occupancy sensor, such as an ultrasonic or passive IR sensor, and an ambient light sensor, such as a photoresistor or a single-pixel sensor that measures light in the room. In some embodiments, the smart nightlight 1670 is configured to activate the light source when its ambient light sensor detects that the room is dark and when its occupancy sensor detects that someone is in the room. In other embodiments, the smart nightlight 1670 is simply configured to activate the light source when its ambient light sensor detects that the room is dark. Further, according to embodiments, the smart nightlight 1670 includes a low-power wireless communication chip (e.g., ZigBee chip) that regularly sends out messages regarding the occupancy of the room and the amount of light in the room, including instantaneous messages coincident with the occupancy sensor detecting the presence of a person in the room. As mentioned above, these messages may be sent wirelessly, using the mesh network, from node to node (i.e., smart device to smart device) within the smart-home environment 1600 as well as over the Internet 1699 to cloud-computing system 1664.

Other examples of low-powered nodes include battery-operated versions of the hazard detectors 1604. These hazard detectors 1604 are often located in an area without access to constant and reliable (e.g., structural) power and, as discussed in detail below, may include any number and type of sensors, such as smoke/fire/heat sensors, carbon monoxide/dioxide sensors, occupancy/motion sensors, ambient light sensors, temperature sensors, humidity sensors, and the like. Furthermore, hazard detectors 1604 can send messages that correspond to each of the respective sensors to the other devices and cloud-computing system 1664, such as by using the mesh network as described above.

Examples of spokesman nodes include smart doorbells 1606, smart thermostats 1602, smart wall switches 1608, and smart wall plugs 1610. These devices 1602, 1606, 1608, and 1610 are often located near and connected to a reliable power source, and therefore can include more power-consuming components, such as one or more communication chips capable of bidirectional communication in any variety of protocols.

In some embodiments, the mesh network of low-powered and spokesman nodes can be used to provide exit lighting in the event of an emergency. In some instances, to facilitate this, users provide pre-configuration information that indicates exit routes in the smart-home environment 1600. For example, for each room in the house, the user provides a map of the best exit route. It should be appreciated that instead of a user providing this information, cloud-computing system 1664 or some other device could automatically determine the routes using uploaded maps, diagrams, architectural drawings of the smart-home house, as well as using a map generated based on positional information obtained from the nodes of the mesh network (e.g., positional information from the devices is used to construct a map of the house). In operation, when an alarm is activated (e.g., when one or more of the hazard detector 1604 detects smoke and activates an alarm), cloud-computing system 1664 or some other device uses occupancy information obtained from the low-powered and spokesman nodes to determine which rooms are occupied and then turns on lights (e.g., smart nightlights 1670, wall switches 1608, smart wall plugs 1610 that power lamps, etc.) along the exit routes from the occupied rooms so as to provide emergency exit lighting.

Further included and illustrated in the exemplary smart-home environment 1600 of FIG. 16 are service robots 1662 each configured to carry out, in an autonomous manner, any of a variety of household tasks. For some embodiments, the service robots 1662 can be respectively configured to perform floor sweeping, floor washing, etc. in a manner similar to that of known commercially available devices such as the Roomba™ and Scooba™ products sold by iRobot, Inc. of Bedford, Mass. Tasks such as floor sweeping and floor washing can be considered as "away" or "while-away" tasks for purposes of the instant description, as it is generally more desirable for these tasks to be performed when the occupants are not present. For other embodiments, one or more of the service robots 1662 are configured to perform tasks such as playing music for an occupant, serving as a localized thermostat for an occupant, serving as a localized air monitor/purifier for an occupant, serving as a localized baby monitor, serving as a localized hazard detector for an occupant, and so forth, it being generally more desirable for such tasks to be carried out in the immediate presence of the human occupant. For purposes of the instant description, such tasks can be considered as "human-facing" or "human-centric" tasks.

When serving as a localized air monitor/purifier for an occupant, a particular service robot 1662 can be considered to be facilitating what can be called a "personal health-area network" for the occupant, with the objective being to keep the air quality in the occupant's immediate space at healthy levels. Alternatively or in conjunction therewith, other health-related functions can be provided, such as monitoring the temperature or heart rate of the occupant (e.g., using finely remote sensors, near-field communication with on-person monitors, etc.). When serving as a localized hazard detector for an occupant, a particular service robot 1662 can be considered to be facilitating what can be called a "personal safety-area network" for the occupant, with the objective being to ensure there is no excessive carbon monoxide, smoke, fire, etc., in the immediate space of the occupant. Methods analogous to those described above for personal comfort-area networks in terms of occupant identifying and tracking are likewise applicable for personal health-area network and personal safety-area network embodiments.

According to some embodiments, the above-referenced facilitation of personal comfort-area networks, personal health-area networks, personal safety-area networks, and/or other such human-facing functionalities of the service robots 1662, are further enhanced by logical integration with other smart sensors in the home according to rules-based inferencing techniques or artificial intelligence techniques for achieving better performance of those human-facing functionalities and/or for achieving those goals in energy-conserving or other resource-conserving ways. Thus, for one embodiment relating to personal health-area networks, the air monitor/purifier service robot 1662 can be configured to detect whether a household pet is moving toward the currently settled location of the occupant (e.g., using on-board sensors and/or by data communications with other smart-home sensors along with rules-based inferencing/artificial intelligence techniques), and if so, the air purifying rate is immediately increased in preparation for the arrival of more airborne pet dander. For another embodiment relating to personal safety-area networks, the hazard detector service robot 1662 can be advised by other smart-home sensors that the temperature and humidity levels are rising in the kitchen, which is nearby the occupant's current dining room location, and responsive to this advisory, the hazard detector service robot 1662 will temporarily raise a hazard detection threshold, such as a smoke detection threshold, under an inference that any small increases in ambient smoke levels will most likely be due to cooking activity and not due to a genuinely hazardous condition.

Figure 17:
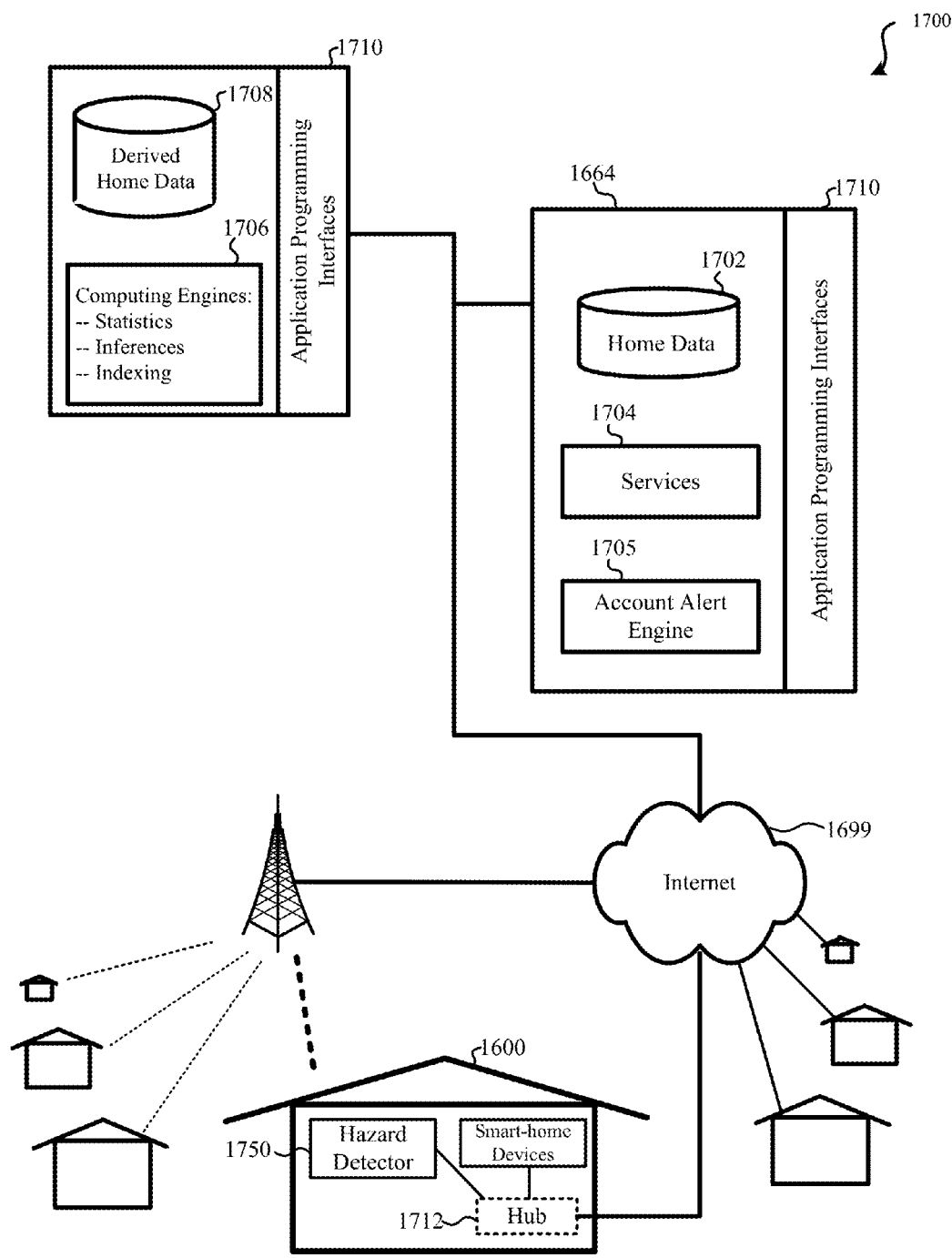
FIG. 17 illustrates a network-level view of the extensible devices and services platform with which a hazard detector may be integrated.

FIG. 17 illustrates a network-level view of an extensible devices and services platform 1700 with which a plurality of smart-home environments, such as the smart-home environment 1600 of FIG. 16, can be integrated. The extensible devices and services platform 1700 includes cloud-computing system 1664. Each of the intelligent, network-connected devices 1602, 1604, 1606, 1608, 1610, 1612, 1614, and 1616 from FIG. 16 may communicate with cloud-computing system 1664. For example, a connection to the Internet 1699 can be established either directly (for example, using 3G/4G connectivity to a wireless carrier), through a hubbed network 1712 (which can be a scheme ranging from a simple wireless router, for example, up to and including an intelligent, dedicated whole-home control node), or through any combination thereof.

Although in some examples provided herein, the devices and services platform 1700 communicates with and collects data from the smart devices of smart-home environment 1600 of FIG. 16, it should be appreciated that the devices and services platform 1700 communicates with and collects data from a plurality of smart-home environments across the world. For example, cloud-computing system 1664 can collect home data 1702 from the devices of one or more smart-home environments, where the devices can routinely transmit home data or can transmit home data in specific instances (e.g., when a device queries the home data 1702). Thus, the devices and services platform 1700 routinely collects data from homes across the world. As described, the collected home data 1702 includes, for example, power consumption data, occupancy data, HVAC settings and usage data, carbon monoxide levels data, carbon dioxide levels data, volatile organic compounds levels data, sleeping schedule data, cooking schedule data, inside and outside temperature humidity data, television viewership data, inside and outside noise level data, etc.

Cloud-computing system 1664 can further provide one or more services 1704. The services 1704 can include, e.g., software updates, customer support, sensor data collection/logging, remote access, remote or distributed control, or use suggestions (e.g., based on collected home data 1702 to improve performance, reduce utility cost, etc.). Data associated with the services 1704 can be stored at cloud-computing system 1664 and cloud-computing system 1664 can retrieve and transmit the data at an appropriate time (e.g., at regular intervals, upon receiving a request from a user, etc.).

As part of services 1704, user accounts may be maintained by the cloud-computing system 1664. The user account may store subscription information, billing information, registration information, user preferences, and/or other data associated with various smart-home devices, such as one or more hazard detectors, installed within a structure that is linked with a user account. Occasionally, attention of a user to his or her user account may be requested. In response to a query from hazard detector 1750 (or other smart-home device), a message may be transmitted by the cloud-computing system 1664 to hazard detector 1750 (which may represent any of the previously described hazard detectors) indicating that a status output by hazard detector 1750 should indicate that a user is requested to log in to his or her user account. Further detail regarding the requested log may be transmitted by service 1704 to hazard detector 1750. For instance, the reason for the requested login may be expired payment information (such as an expired credit card). The user can request detail on a status output by hazard detector 1750, which may be presented to the user as a color and animation output via a light of hazard detector 1750. The request for detail may be by performing a gesture within the vicinity of hazard detector 1750. A spoken message may then be output by hazard detector 1750 indicating that the user is requested to log in to his account and may also indicate the reason of the payment information needing to be updated. As such, a status check performed by hazard detector 1750 may not only check the status of hazard detector 1750 itself, but also the state of a remotely-maintained user account.

As illustrated in FIG. 17, an embodiment of the extensible devices and services platform 1700 includes a processing engine 1706, which can be concentrated at a single server or distributed among several different computing entities without limitation. The processing engine 1706 can include computerized engines (e.g., software executed by hardware) configured to receive data from devices of smart-home environments (e.g., via the Internet or a hubbed network), to index the data, to analyze the data and/or to generate statistics based on the analysis or as part of the analysis. The analyzed data can be stored as derived home data 1708.

Results of the analysis or statistics can thereafter be transmitted back to the device that provided home data used to derive the results, to other devices, to a server providing a webpage to a user of the device, or to other non-device entities. For example, use statistics, use statistics relative to use of other devices, use patterns, and/or statistics summarizing sensor readings can be generated by the processing engine 1706 and transmitted. The results or statistics can be provided via the Internet 1699. In this manner, the processing engine 1706 can be configured and programmed to derive a variety of useful information from the home data 1702. A single server can include one or more engines.

In some embodiments, to encourage innovation and research and to increase products and services available to users, the devices and services platform 1700 exposes a range of application programming interfaces (APIs) 1710 to third parties, such as charities, governmental entities (e.g., the Food and Drug Administration or the Environmental Protection Agency), academic institutions (e.g., university researchers), businesses (e.g., providing device warranties or service to related equipment, targeting advertisements based on home data), utility companies, and other third parties. The APIs 1710 may be coupled to and permit third-party systems to communicate with cloud-computing system 1664, including the services 1704, the processing engine 1706, the home data 1702, and the derived home data 1708. For example, the APIs 1710 allow applications executed by the third parties to initiate specific data processing tasks that are executed by cloud-computing system

1664, as well as to receive dynamic updates to the home data 1702 and the derived home data 1708.

Account alert engine may serve to determine whether a hazard detector should provide an indication that the user's account requires attention. For instance, account alert engine 1705 may periodically assess the state of a user's account, such as whether settings need updating, whether payment information is up-to-date, whether one or more messages are pending, whether payment is due, etc. If user attention is required, upon a request being received from a hazard detector and a look-up of the user's account being performed, account alert engine may respond with an indication that the user account requires attention. Additional detail may also be provided such that if the user performs a gesture or otherwise requests additional detail, such detail can be provided, such as via an auditory message. If user attention is not required, upon a request being received from a hazard detector and a look-up of the user's account being performed (e.g., by determining an account associated with the hazard detector from which the request was received), account alert engine may respond with an indication that the user account does not require attention.

FIG. 1800 illustrates an abstracted functional view of the extensible devices and services platform 1700 of FIG. 17, with particular reference to the processing engine 1706 as well as devices, such as those of the smart-home environment 1600 of FIG. 16. Even though devices situated in smart-home environments will have an endless variety of different individual capabilities and limitations, they can all be thought of as sharing common characteristics in that each of them is a data consumer 1865 (DC), a data source 1866 (DS), a services consumer 1867 (SC), and a services source 1868 (SS). Advantageously, in addition to providing the essential control information needed for the devices to achieve their local and immediate objectives, the extensible devices and services platform 1700 can also be configured to harness the large amount of data that is flowing out of these devices. In addition to enhancing or optimizing the actual operation of the devices themselves with respect to their immediate functions, the extensible devices and services platform 1700 can be directed to "repurposing" that data in a variety of automated, extensible, flexible, and/or scalable ways to achieve a variety of useful objectives. These objectives may be predefined or adaptively identified based on, e.g., usage patterns, device efficiency, and/or user input (e.g., requesting specific functionality).

Figure 18:
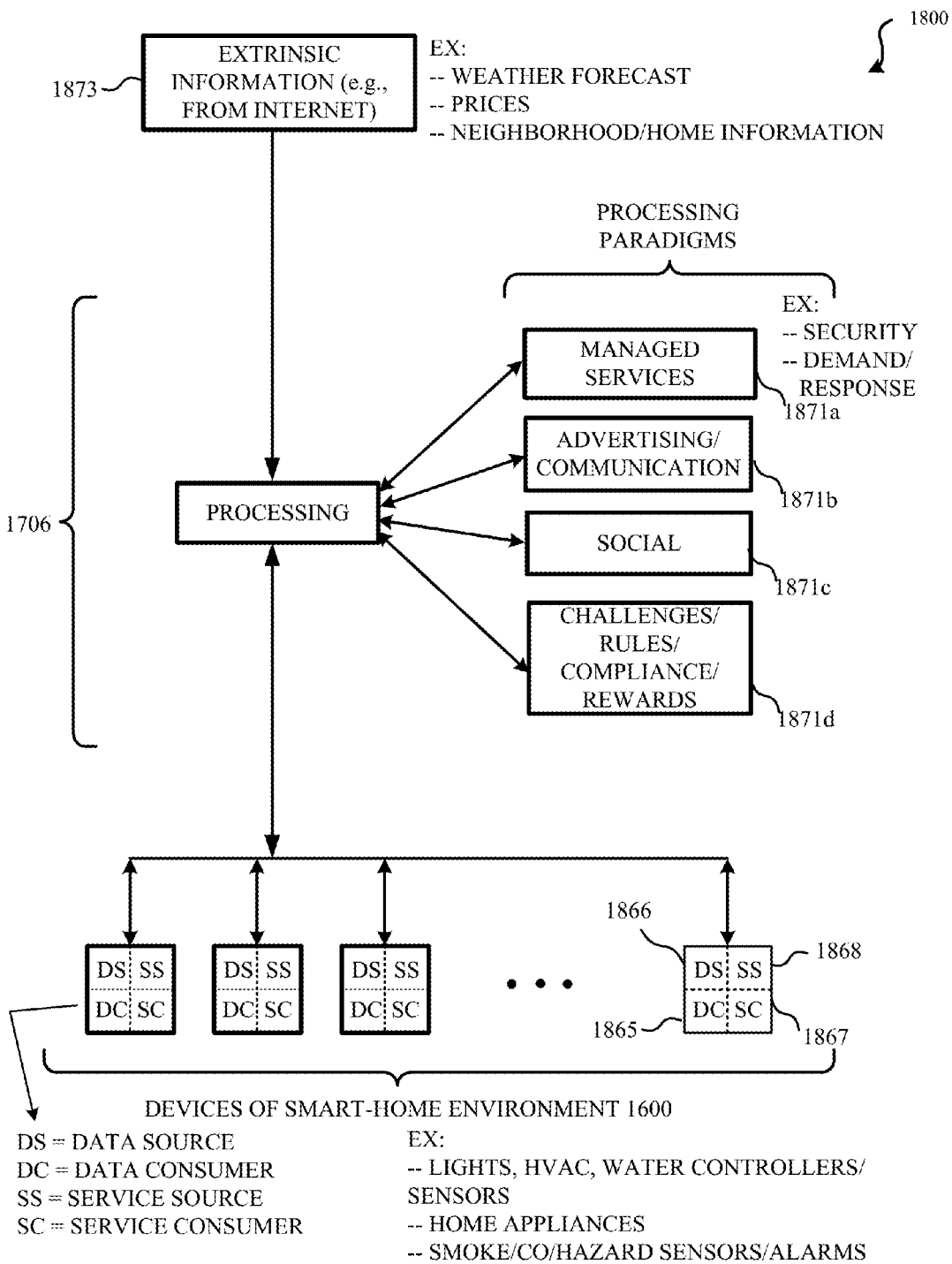
FIG. 18 illustrates an embodiment of an abstracted functional view of the extensible devices and services platform of FIG. 17, with reference to a processing engine as well as devices of the smart-home environment.

For example, FIG. 18 shows processing engine 1706 as including a number of paradigms 1871. Processing engine 1706 can include a managed services paradigm 1871*a* that monitors and manages primary or secondary device functions. The device functions can include ensuring proper operation of a device given user inputs, estimating that (e.g., and responding to an instance in which) an intruder is or is attempting to be in a dwelling, detecting a failure of equipment coupled to the device (e.g., a light bulb having burned out), implementing or otherwise responding to energy demand response events, or alerting a user of a current or predicted future event or characteristic. Processing engine 1706 can further include an advertising/communication paradigm 1871*b* that estimates characteristics (e.g., demographic information), desires and/or products of interest of a user based on device usage. Services, promotions, products or upgrades can then be offered or automatically provided to the user. Processing engine 1706 can further include a social paradigm 1871*c* that uses information from a social network, provides information to a social network (for example, based on device usage), and/or processes data associated with user and/or device interactions with the social network platform. For example, a user's status as reported to his trusted contacts on the social network could be updated to indicate when he is home based on light detection, security system inactivation or device usage detectors. As another example, a user may be able to share device-usage statistics with other users. In yet another example, a user may share HVAC settings that result in low power bills and other users may download the HVAC settings to their smart thermostat 1602 to reduce their power bills.

The processing engine 1706 can include a challenges/rules/compliance/rewards paradigm 1871*d* that informs a user of challenges, competitions, rules, compliance regulations and/or rewards and/or that uses operation data to determine whether a challenge has been met, a rule or regulation has been complied with and/or a reward has been earned. The challenges, rules or regulations can relate to efforts to conserve energy, to live safely (e.g., reducing exposure to toxins or carcinogens), to conserve money and/or equipment life, to improve health, etc. For example, one challenge may involve participants turning down their thermostat by one degree for one week. Those that successfully complete the challenge are rewarded, such as by coupons, virtual currency, status, etc. Regarding compliance, an example involves a rental-property owner making a rule that no renters are permitted to access certain owner's rooms. The devices in the room having occupancy sensors could send updates to the owner when the room is accessed.

The processing engine 1706 can integrate or otherwise utilize extrinsic information 1873 from extrinsic sources to improve the functioning of one or more processing paradigms. Extrinsic information 1873 can be used to interpret data received from a device, to determine a characteristic of the environment near the device (e.g., outside a structure that the device is enclosed in), to determine services or products available to the user, to identify a social network or social-network information, to determine contact information of entities (e.g., public-service entities such as an emergency-response team, the police or a hospital) near the device, etc., to identify statistical or environmental conditions, trends or other information associated with a home or neighborhood, and so forth.

An extraordinary range and variety of benefits can be brought about by, and fit within the scope of, the described extensible devices and services platform 1700A, ranging from the ordinary to the profound. Thus, in one "ordinary" example, each bedroom of the smart-home environment 1600 can be provided with a smart wall switch 1608, a smart wall plug 1610, and/or smart hazard detectors 1604, all or some of which include an occupancy sensor, wherein the occupancy sensor is also capable of inferring (e.g., by virtue of motion detection, facial recognition, audible sound patterns, etc.) whether the occupant is asleep or awake. If a serious fire event is sensed, the remote security/monitoring service or fire department is advised of how many occupants there are in each bedroom, and whether those occupants are still asleep (or immobile) or whether they have properly evacuated the bedroom. While this is, of course, a very advantageous capability accommodated by the described extensible devices and services platform, there can be substantially more "profound" examples that can truly illustrate the potential of a larger "intelligence" that can be made available. By way of perhaps a more "profound" example, the same bedroom occupancy data that is being used for fire safety can also be "repurposed" by the processing engine 1706 in the context of a social paradigm of neighborhood child development and education. Thus, for example, the same bedroom occupancy and motion data discussed in the "ordinary" example can be collected and made available (properly anonymized) for processing in which the sleep patterns of schoolchildren in a particular ZIP code can be identified and tracked. Localized variations in the sleeping patterns of the schoolchildren may be identified and correlated, for example, to different nutrition programs in local schools.

Figure 19:
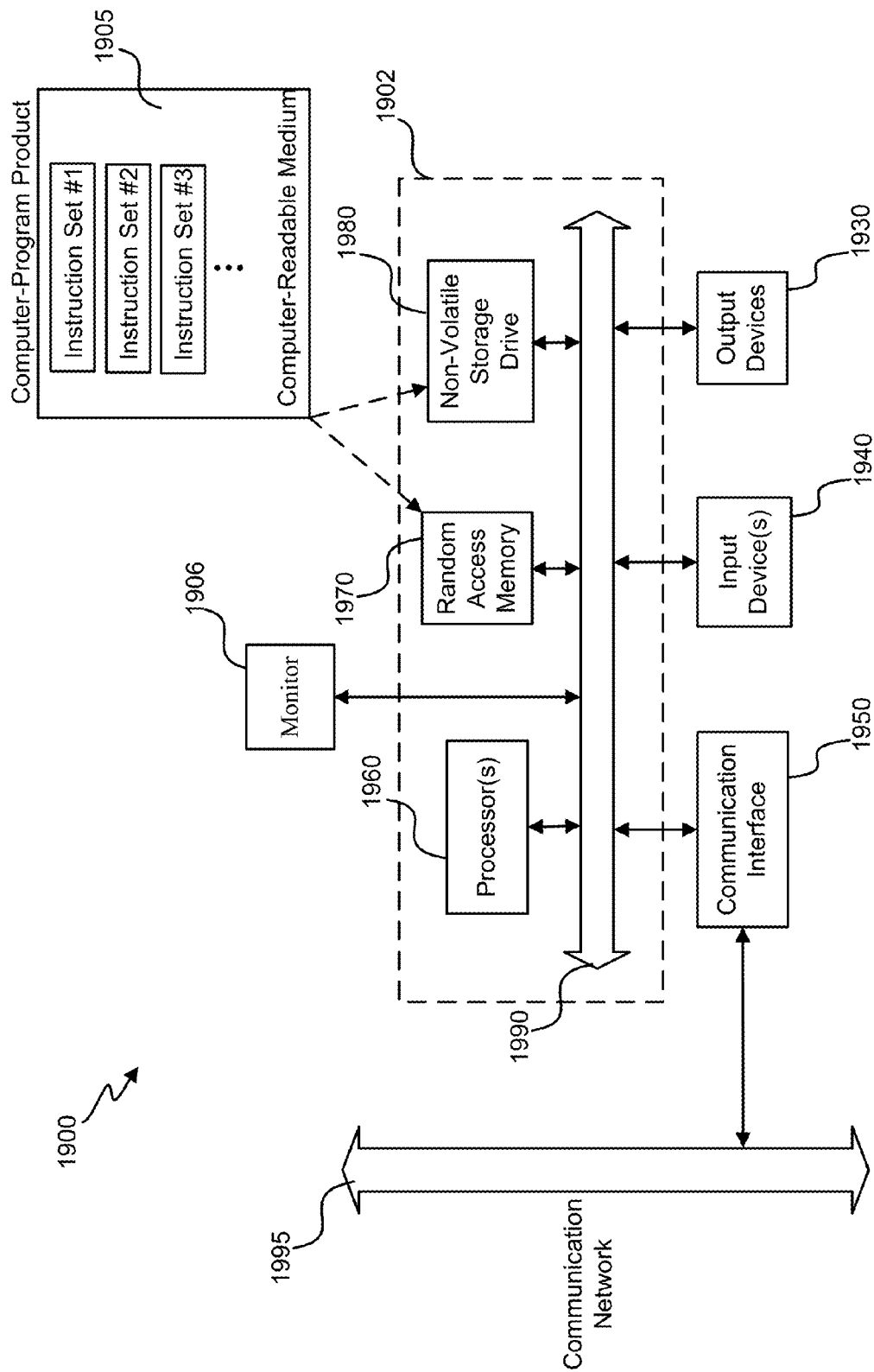
FIG. 19 illustrates an embodiment of a computer system.

With reference to FIG. 19, an embodiment of a special-purpose computer system 1900 is shown. For example, one or more intelligent components, processing system 110 and components thereof may be a special-purpose computer system 1900. Such a special-purpose computer system 1900 may be incorporated as part of a hazard detector and/or any of the other computerized devices discussed herein, such as a remote server, smart thermostat, or network. The above methods may be implemented by computer-program products that direct a computer system to perform the actions of the above-described methods and components. Each such computer-program product may comprise sets of instructions (codes) embodied on a computer-readable medium that direct the processor of a computer system to perform corresponding actions. The instructions may be configured to run in sequential order, or in parallel (such as under different processing threads), or in a combination thereof. After loading the computer-program products on a general purpose computer system 1926, it is transformed into the special-purpose computer system 1900.

Special-purpose computer system 1900 comprises a computer 1902, a monitor 1906 coupled to computer 1902, one or more additional user output devices 1930 (optional) coupled to computer 1902, one or more user input devices 1940 (e.g., keyboard, mouse, track ball, touch screen) coupled to computer 1902, an optional communications interface 1950 coupled to computer 1902, a computer-program product 1905 stored in a tangible computer-readable memory in computer 1902. Computer-program product 1905 directs computer system 1900 to perform the above-described methods. Computer 1902 may include one or more processors 1960 that communicate with a number of peripheral devices via a bus subsystem 1990. These peripheral devices may include user output device(s) 1930, user input device(s) 1940, communications interface 1950, and a storage subsystem, such as random access memory (RAM) 1970 and non-volatile storage drive 1980 (e.g., disk drive, optical drive, solid state drive), which are forms of tangible computer-readable memory.

Computer-program product 1905 may be stored in non-volatile storage drive 1980 or another computer-readable medium accessible to computer 1902 and loaded into random access memory (RAM) 1970. Each processor 1960 may comprise a microprocessor, such as a microprocessor from Intel® or Advanced Micro Devices, Inc.®, or the like. To support computer-program product 1905, the computer 1902 runs an operating system that handles the communications of computer-program product 1905 with the above-noted components, as well as the communications between the above-noted components in support of the computer-program product 1905. Exemplary operating systems include Windows® or the like from Microsoft Corporation, Solaris® from Sun Microsystems, LINUX, UNIX, and the like.

User input devices 1940 include all possible types of devices and mechanisms to input information to computer 1902. These may include a keyboard, a keypad, a mouse, a scanner, a digital drawing pad, a touch screen incorporated into the display, audio input devices such as voice recognition systems, microphones, and other types of input devices. In various embodiments, user input devices 1940 are typically embodied as a computer mouse, a trackball, a track pad, a joystick, wireless remote, a drawing tablet, a voice command system. User input devices 1940 typically allow a user to select objects, icons, text and the like that appear on the monitor 1906 via a command such as a click of a button or the like. User output devices 1930 include all possible types of devices and mechanisms to output information from computer 1902. These may include a display (e.g., monitor 1906), printers, non-visual displays such as audio output devices, etc.

Communications interface 1950 provides an interface to other communication networks, such as communication network 1995, and devices and may serve as an interface to receive data from and transmit data to other systems, WANs and/or the Internet. Embodiments of communications interface 1950 typically include an Ethernet card, a modem (telephone, satellite, cable, ISDN), a (asynchronous) digital subscriber line (DSL) unit, a FireWire® interface, a USB® interface, a wireless network adapter, and the like. For example, communications interface 1950 may be coupled to a computer network, to a FireWire® bus, or the like. In other embodiments, communications interface 1950 may be physically integrated on the motherboard of computer 1902, and/or may be a software program, or the like.

RAM 1970 and non-volatile storage drive 1980 are examples of tangible computer-readable media configured to store data such as computer-program product embodiments of the present invention, including executable computer code, human-readable code, or the like. Other types of tangible computer-readable media include floppy disks, removable hard disks, optical storage media such as CD-ROMs, DVDs, bar codes, semiconductor memories such as flash memories, read-only-memories (ROMs), battery-backed volatile memories, networked storage devices, and the like. RAM 1970 and non-volatile storage drive 1980 may be configured to store the basic programming and data constructs that provide the functionality of various embodiments of the present invention, as described above.

Software instruction sets that provide the functionality of the present invention may be stored in RAM 1970 and non-volatile storage drive 1980. These instruction sets or code may be executed by the processor(s) 1960. RAM 1970 and non-volatile storage drive 1980 may also provide a repository to store data and data structures used in accordance with the present invention. RAM 1970 and non-volatile storage drive 1980 may include a number of memories including a main random access memory (RAM) to store instructions and data during program execution and a read-only memory (ROM) in which fixed instructions are stored. RAM 1970 and non-volatile storage drive 1980 may include a file storage subsystem providing persistent (non-volatile) storage of program and/or data files. RAM 1970 and non-volatile storage drive 1980 may also include removable storage systems, such as removable flash memory.

Bus subsystem 1990 provides a mechanism to allow the various components and subsystems of computer 1902 to communicate with each other as intended. Although bus subsystem 1990 is shown schematically as a single bus, alternative embodiments of the bus subsystem may utilize multiple busses or communication paths within the computer 1902.

It should be noted that the methods, systems, and devices discussed above are intended merely to be examples. It must be stressed that various embodiments may omit, substitute, or add various procedures or components as appropriate. For instance, it should be appreciated that, in alternative embodiments, the methods may be performed in an order different from that described, and that various steps may be added, omitted, or combined. Also, features described with respect to certain embodiments may be combined in various other embodiments. Different aspects and elements of the embodiments may be combined in a similar manner. Also, it should be emphasized that technology evolves and, thus, many of the elements are examples and should not be interpreted to limit the scope of the invention.

Specific details are given in the description to provide a thorough understanding of the embodiments. However, it will be understood by one of ordinary skill in the art that the embodiments may be practiced without these specific details. For example, well-known, processes, structures, and techniques have been shown without unnecessary detail in order to avoid obscuring the embodiments. This description provides example embodiments only, and is not intended to limit the scope, applicability, or configuration of the invention. Rather, the preceding description of the embodiments will provide those skilled in the art with an enabling description for implementing embodiments of the invention. Various changes may be made in the function and arrangement of elements without departing from the spirit and scope of the invention.

Also, it is noted that the embodiments may be described as a process which is depicted as a flow diagram or block diagram. Although each may describe the operations as a sequential process, many of the operations can be performed in parallel or concurrently. In addition, the order of the operations may be rearranged. A process may have additional steps not included in the figure.

Having described several embodiments, it will be recognized by those of skill in the art that various modifications, alternative constructions, and equivalents may be used without departing from the spirit of the invention. For example, the above elements may merely be a component of a larger system, wherein other rules may take precedence over or otherwise modify the application of the invention. Also, a number of steps may be undertaken before, during, or after the above elements are considered. Accordingly, the above description should not be taken as limiting the scope of the invention.

What is claimed is:

1. A smart home device, comprising:
    a case, the case having an interior and an exterior surface, wherein the interior of the case houses components of the smart home device;
    a user input component;
    one or more environmental sensors housed in the interior of the case, wherein the one or more environmental sensors detect the presence of one or more types of environmental conditions;
    a light that emits light, the light comprising a plurality of lighting elements, wherein:
        the light is capable of illuminating in a plurality of colors and in a plurality of animation patterns; and
        the light and the case are arranged such that light emitted by the light is emitted around an edge of the user input component and reflects off the exterior surface of the case into an ambient environment of the smart home device; and
    a processing system in communication with the one or more environmental sensors and the light, the processing system comprising at least one processor that is configured to:
        determine a state of the smart home device; and
        cause the light to illuminate using at least one color of the plurality of colors and an animation pattern of the plurality of animation patterns in response to the determined state of the smart home device.

2. The smart home device of claim 1, wherein when each of the plurality of lighting elements are illuminated, light output by the light creates a continuous ring of light reflected off of the exterior surface of the case.

3. The smart home device of claim 1, further comprising a presence sensor wherein the processing system is in communication with the presence sensor and the processing system is further configured to:
    receive information indicative of a user presence from the presence sensor while causing the light to illuminate using the at least one color and the animation pattern; and
    alter the animation pattern used to illuminate the light in response to receiving the information indicative of the user presence.

4. The smart home device of claim 1, further comprising a microphone wherein the processing system is in communication with the microphone and the processing system is further configured to:
    receive audio data from the microphone while causing the light to illuminate using at least one color; and
    modulate illumination of the light based on the received audio data from the microphone.

5. The smart home device of claim 4, wherein the processing system being configured to modulate illumination of the light based on the received audio data from the microphone comprises the processing system being configured to module illumination of the light based on a volume of a user's voice received by the microphone.

6. The smart home device of claim 1, wherein the processing system is further configured to:
    access a stored lookup table that relates a plurality of states to the plurality of colors and the plurality of animation patterns; and
    identify the at least one color associated with the determined state and the animation pattern associated with the determined state.

7. The smart home device of claim 1, wherein the plurality of animation patterns comprise:
    a rotating animation in which lighting elements of the plurality of lighting elements are sequentially increased and decreased in brightness; and
    a shimmer animation in which light elements of the plurality of lighting elements are cycled through a hue range pattern.

8. The smart home device of claim 1, wherein the light comprises:
    a light ring that receives and disperses light generated by the plurality of lighting elements.

9. The smart home device of claim 1, further comprising a passive infrared (PIR) detector, wherein the PIR detector is configured to sense infrared light through a user input component of the smart home device that functions as a lens.

10. A method for illuminating a light of a smart home device, the method comprising:
    determining, by the smart home device, a state of the smart home device based at least in part on measurements from one or more environmental sensors;
    accessing, by the smart home device, a stored lookup table that relates a plurality of states of the smart home device to: 1) a plurality of colors, and 2) a plurality of animations;

identifying, by the smart home device, using the stored lookup table, at least one color associated with the determined state and an animation pattern associated with the determined state; and causing, by the smart home device, the light of the smart home device to illuminate using the identified at least one color and the identified animation pattern, wherein light emitted by the light is emitted around a user input component and reflects off an exterior surface of a case of the smart home device into an ambient environment of the smart home device.

11. The method for illuminating the light of the smart home device of claim 10, wherein causing the light of the smart home device to illuminate comprises:
   encircling the user input component with light output by the light using the identified at least one color and the identified animation pattern.

12. The method for illuminating the light of the smart home device of claim 10, wherein causing the light of the smart home device to illuminate comprises:
   causing a continuous ring of light to reflect off the exterior surface of the case.

13. The method for illuminating the light of the smart home device of claim 10, further comprising:
   obtaining, by the smart home device, information indicative of a user presence while causing the light to illuminate using the at least one color and the animation pattern; and
   setting, by the smart home device, the identified animation pattern used to illuminate the light based on receiving the information indicative of the user presence.

14. The method for illuminating the light of the smart home device of claim 10, further comprising:
   capturing, by the smart home device, audio data while causing the light to illuminate using the at least one color and the animation pattern; and
   modulating, by the smart home device, illumination of the light based on the captured audio data.

15. The method for illuminating the light of the smart home device of claim 10, wherein causing the light to illuminate comprises:
   causing the light to illuminate using a rotating animation, wherein the rotating animation comprises illuminating a plurality of lighting elements of the light sequentially.

* * * * *

UNITED STATES PATENT AND TRADEMARK OFFICE
CERTIFICATE OF CORRECTION

PATENT NO. : 10,032,343 B2
APPLICATION NO. : 15/438076
DATED : July 24, 2018
INVENTOR(S) : Jeffrey A. Boyd et al.

Page 1 of 1

It is certified that error appears in the above-identified patent and that said Letters Patent is hereby corrected as shown below:

In the Claims

Column 38, Line 33, Claim 5: replace "module" with --modulate--.

Signed and Sealed this
Second Day of October, 2018

Andrei Iancu
*Director of the United States Patent and Trademark Office*